(12) United States Patent
Lee et al.

US009763577B2

(10) Patent No.: US 9,763,577 B2
(45) Date of Patent: Sep. 19, 2017

(54) IMAGING AGENT FOR DETECTION OF DISEASED CELLS

(71) Applicant: Lumicell, Inc., Wellesley, MA (US)

(72) Inventors: W. David Lee, Brookline, MA (US); Moungi G. Bawendi, Cambridge, MA (US); Jorge Ferrer, Arlington, MA (US)

(73) Assignee: Lumicell, Inc., Wellesley, MA (US)

( * ) Notice: Subject to any disclaimer, the term of this patent is extended or adjusted under 35 U.S.C. 154(b) by 184 days.

(21) Appl. No.: 14/211,014

(22) Filed: Mar. 14, 2014

(65) Prior Publication Data

US 2014/0301950 A1   Oct. 9, 2014

Related U.S. Application Data

(60) Provisional application No. 61/781,601, filed on Mar. 14, 2013, provisional application No. 61/785,136, filed on Mar. 14, 2013.

(51) Int. Cl.
| | |
|---|---|
| *A61B 5/00* | (2006.01) |
| *A61B 8/00* | (2006.01) |
| *A61B 10/00* | (2006.01) |
| *A61K 49/00* | (2006.01) |
| *A61B 90/00* | (2016.01) |
| *A61B 90/30* | (2016.01) |

(52) U.S. Cl.
CPC .......... *A61B 5/0091* (2013.01); *A61B 5/0071* (2013.01); *A61B 5/0075* (2013.01); *A61B 5/0086* (2013.01); *A61B 5/4312* (2013.01); *A61B 10/0041* (2013.01); *A61B 90/361* (2016.02); *A61K 49/0032* (2013.01); *A61K 49/0056* (2013.01); *A61B 5/6886* (2013.01); *A61B 2090/306* (2016.02); *A61B 2090/309* (2016.02); *A61B 2090/3616* (2016.02); *A61B 2090/3941* (2016.02); *A61B 2505/05* (2013.01); *A61B 2560/0431* (2013.01)

(58) Field of Classification Search
CPC .................................................. A61B 5/0091
USPC ...................................................... 424/9.6
See application file for complete search history.

(56) References Cited

U.S. PATENT DOCUMENTS

| | | | |
|---|---|---|---|
| 5,268,486 A | 12/1993 | Waggoner et al. |
| 5,366,860 A | 11/1994 | Bergot et al. |
| 5,438,989 A | 8/1995 | Hochman et al. |
| 5,569,587 A | 10/1996 | Waggoner |
| 5,593,658 A | 1/1997 | Bogdanov et al. |
| 5,647,368 A | 7/1997 | Zeng et al. |
| 5,688,221 A | 11/1997 | Yabe et al. |
| 5,749,830 A | 5/1998 | Kaneko |
| 5,769,791 A | 6/1998 | Benaron et al. |
| 5,800,995 A | 9/1998 | Patonay et al. |
| 5,954,634 A | 9/1999 | Igarashi |
| 5,968,479 A | 10/1999 | Ito et al. |
| 6,027,709 A | 2/2000 | Little et al. |
| 6,083,486 A | 7/2000 | Weissleder et al. |
| 6,136,612 A | 10/2000 | Della Ciana et al. |
| 6,180,086 B1 | 1/2001 | Achilefu et al. |
| 6,256,530 B1 | 7/2001 | Wolfe |
| 6,485,413 B1 | 11/2002 | Boppart et al. |
| 6,537,211 B1 | 3/2003 | Wang et al. |
| 6,592,847 B1 | 7/2003 | Weissleder et al. |
| 6,620,621 B1 | 9/2003 | Cohenford et al. |
| 6,631,230 B1 | 10/2003 | Campbell |
| 6,667,159 B1 | 12/2003 | Walt et al. |
| 6,737,247 B2 | 5/2004 | Bogdanov et al. |
| 6,834,238 B1 | 12/2004 | Hochman |
| 7,128,894 B1 | 10/2006 | Tannous et al. |
| 7,285,089 B2 | 10/2007 | Viellerobe et al. |
| 7,383,076 B2 | 6/2008 | Ntziachristos et al. |
| 7,383,077 B2 | 6/2008 | Zeng |
| 7,452,727 B2 | 11/2008 | Hennig et al. |
| 7,498,029 B2 | 3/2009 | Hasan et al. |
| 8,815,214 B2 | 8/2014 | Rajopadhye et al. |
| 8,983,581 B2 | 3/2015 | Bawendi et al. |
| 9,032,965 B2 | 5/2015 | Lee |
| 9,155,471 B2 | 10/2015 | Lee |
| 9,314,304 B2 | 4/2016 | Lee et al. |
| 2002/0064794 A1 | 5/2002 | Leung et al. |
| 2002/0115862 A1 | 8/2002 | Czerney et al. |
| 2002/0165456 A1 | 11/2002 | Canpolat et al. |
| 2003/0039741 A1 | 2/2003 | Carver et al. |
| 2003/0044353 A1 | 3/2003 | Weissleder et al. |
| 2003/0138378 A1 | 7/2003 | Hashimshony |
| 2004/0015062 A1 | 1/2004 | Ntziachristos et al. |
| 2004/0071332 A1 | 4/2004 | Bruce et al. |
| 2004/0253593 A1 | 12/2004 | Cai et al. |
| 2005/0130167 A1 | 6/2005 | Bao et al. |

(Continued)

FOREIGN PATENT DOCUMENTS

| | | |
|---|---|---|
| EP | 1065250 A1 | 1/2001 |
| EP | 1211294 A1 | 6/2002 |

(Continued)

OTHER PUBLICATIONS

Cuneo et al. Int J. Radiat. Oncol.; 2013, 86, 136-142.*
ClinicalTrails.gov (https://clinicaltrials.gov/archive/NCT01626066/2012_06_21), 2012, 1-3.*
Brigman Presentation, 2013, 1-29.*
Extended European Search Report for European Application No. 11844820.8 dated Jul. 15, 2014.
International Preliminary Report on Patentability for PCT/US2011/062527 dated Jun. 13, 2013.
International Search Report and Written Opinion for PCT/US2011/062527 dated Jun. 15, 2012.
International Search Report and Written Opinion for PCT/US2010/036433 dated Sep. 6, 2010.
International Preliminary Report on Patentability for PCT/US2010/036433 dated Dec. 8, 2011.

(Continued)

*Primary Examiner* — Michael G Hartley
*Assistant Examiner* — Sean R Donohue
(74) *Attorney, Agent, or Firm* — Wolf, Greenfield & Sacks, P.C.

(57) ABSTRACT

The present invention provides compositions and methods for imaging, for example, tumor resections.

21 Claims, 8 Drawing Sheets

(56) References Cited

U.S. PATENT DOCUMENTS

| | | | |
|---|---|---|---|
| 2005/0171434 A1 | 8/2005 | Madden et al. | |
| 2005/0207668 A1 | 9/2005 | Perchant et al. | |
| 2005/0214221 A1 | 9/2005 | Poss et al. | |
| 2006/0009590 A1* | 1/2006 | Kozlowski et al. | 525/374 |
| 2006/0165350 A1 | 7/2006 | Gelikonov et al. | |
| 2006/0188797 A1 | 8/2006 | Roy et al. | |
| 2006/0253107 A1 | 11/2006 | Hashimshony et al. | |
| 2007/0036725 A1 | 2/2007 | Bogyo et al. | |
| 2007/0160279 A1 | 7/2007 | Demos | |
| 2007/0179174 A1 | 8/2007 | Bachurin et al. | |
| 2007/0182959 A1 | 8/2007 | Maier et al. | |
| 2007/0255169 A1 | 11/2007 | Hashimshony et al. | |
| 2007/0260156 A1 | 11/2007 | Hashimshony | |
| 2008/0015446 A1 | 1/2008 | Mahmood et al. | |
| 2008/0029711 A1 | 2/2008 | Viellerobe et al. | |
| 2008/0039742 A1 | 2/2008 | Hashimshony et al. | |
| 2008/0076674 A1 | 3/2008 | Litman et al. | |
| 2008/0103373 A1 | 5/2008 | Matter et al. | |
| 2008/0154102 A1 | 6/2008 | Frangioni et al. | |
| 2008/0193373 A1 | 8/2008 | Stritzker et al. | |
| 2008/0193431 A1 | 8/2008 | Zheng et al. | |
| 2008/0260646 A1 | 10/2008 | Keller et al. | |
| 2008/0287750 A1 | 11/2008 | Hashimshony et al. | |
| 2009/0004116 A1 | 1/2009 | Bhaumik et al. | |
| 2009/0028788 A1 | 1/2009 | Achilefu | |
| 2009/0123381 A1 | 5/2009 | Hsieh et al. | |
| 2009/0299196 A1 | 12/2009 | Bawendi et al. | |
| 2010/0189658 A1* | 7/2010 | Wendt et al. | 424/9.6 |
| 2010/0262017 A1 | 10/2010 | Frangioni et al. | |
| 2010/0286044 A1 | 11/2010 | Litman et al. | |
| 2010/0298554 A1 | 11/2010 | Laikhter et al. | |
| 2010/0321772 A1 | 12/2010 | Reimer et al. | |
| 2011/0009694 A1 | 1/2011 | Schultz et al. | |
| 2011/0021908 A1 | 1/2011 | Lee et al. | |
| 2011/0028790 A1 | 2/2011 | Farr et al. | |
| 2011/0042580 A1 | 2/2011 | Wilson et al. | |
| 2011/0104071 A1* | 5/2011 | Lee et al. | 424/9.6 |
| 2011/0159566 A1* | 6/2011 | Josephson et al. | 435/188 |
| 2012/0150164 A1 | 6/2012 | Lee et al. | |
| 2014/0207126 A1 | 7/2014 | Bianchi | |
| 2014/0207129 A1 | 7/2014 | Lee et al. | |
| 2014/0243934 A1 | 8/2014 | Vo-Dinh et al. | |
| 2014/0276102 A1 | 9/2014 | Lee et al. | |
| 2014/0276103 A1 | 9/2014 | Lee et al. | |
| 2015/0216416 A1 | 8/2015 | Bawendi et al. | |
| 2015/0216600 A1 | 8/2015 | Lee et al. | |
| 2016/0025632 A1 | 1/2016 | Lee et al. | |

FOREIGN PATENT DOCUMENTS

| | | |
|---|---|---|
| EP | 1223197 A2 | 7/2002 |
| EP | 1273584 A1 | 1/2003 |
| WO | WO 97/13810 A1 | 4/1997 |
| WO | WO 98/47538 A2 | 10/1998 |
| WO | WO 00/53678 A1 | 9/2000 |
| WO | WO 01/90253 A1 | 11/2001 |
| WO | WO 02/24815 A1 | 3/2002 |
| WO | WO 02/056670 A2 | 7/2002 |
| WO | WO 03/105814 A1 | 12/2003 |
| WO | WO 2008/088865 A2 | 7/2008 |

OTHER PUBLICATIONS

International Search Report and Written Opinion for PCT/US2014/027287 dated Jul. 18, 2014.

International Preliminary Report on Patentability for PCT/US2014/027287 dated Sep. 24, 2015.

Invitation to Pay Additional Fees for PCT/US2014/027769 dated Aug. 14, 2014.

International Search Report and Written Opinion for PCT/US2014/027769 dated Oct. 30, 2014.

International Preliminary Report on Patentability for PCT/US2014/027769 dated Sep. 24, 2015.

[No Author Listed], Cathepsin Activatable Fluorescent Probe. Clinical Trials. Jun. 21, 2012. (https://clinicaltrials.gov/archive/NCT01626066/2012_06_21) [last accessed May 27, 2015].

Anikijenko et al., In vivo detection of small subsurface melanomas in athymic mice using noninvasive fiber optic confocal imaging. J Invest Dermatol. Dec. 2001;117(6):1442-8.

Bates et al., Short-range spectroscopic ruler based on a single-molecule optical switch. Phys Rev Lett. Mar. 18, 2005;94(10):108101. Epub Mar. 15, 2005.

Bigio et al., Diagnosis of breast cancer using elastic-scattering spectroscopy: preliminary clinical results. J Biomed Opt. Apr. 2000;5(2):221-8.

Blum et al., Noninvasive optical imaging of cysteine protease activity using fluorescently quenched activity-based probes. Nat Chem Biol. Oct. 2007;3(10):668-77. Epub Sep. 9, 2007.

Bogdanov, Jr. et al., Long-circulating blood pool imaging agents. Adv Drug Del Rev. 1995;16:335-48.

Brigman, Preliminary Analysis of Phase 1, First-In-Human, Cathepsin Activated Tumor Imaging Probe. Presentation. Nov. 2013. 29 pages.

Cheng et al., Near-infrared fluorescent RGD peptides for optical imaging of integrin alphavbeta3 expression in living mice. Bioconjug Chem. Nov.-Dec. 2005;16(6):1433-41.

Cuneo et al., Imaging primary mouse sarcomas after radiation therapy using cathepsin-activatable fluorescent imaging agents. Int J Radiat Oncol Biol Phys. May 1, 2013;86(1):136-42. doi: 10.1016/j.ijrobp.2012.12.007. Epub Feb. 4, 2013.

De Grand et al., Tissue-like phantoms for near-infrared fluorescence imaging system assessment and the training of surgeons. J Biomed Opt. Jan.-Feb. 2006;11(1):014007.

Demos et al., Near-infrared autofluorescence imaging for detection of cancer. J Biomed Opt. May-Jun. 2004;9(3):587-92.

Freireich et al., Quantitative comparison of toxicity of anticancer agents in mouse, rat, hamster, dog, monkey, and man. Cancer Chemother Rep. May 1966;50(4):219-44.

Funovics et al., Protease sensors for bioimaging. Anal Bioanal Chem. Nov. 2003;377(6):956-63. Epub Sep. 3, 2003.

Geigy Pharmaceuticals, Body Surface Area of Adults. In: Scientific Tables. Diem and Lentner, Ed., Ciba-Geigy Ltd. Ardsley, New York. 1970:537.

Goldberg et al., Radiofrequency tissue ablation: importance of local temperature along the electrode tip exposure in determining lesion shape and size. Acad Radiol. Mar. 1996;3(3):212-8.

Graves et al., A submillimeter resolution fluorescence molecular imaging system for small animal imaging. Med Phys. May 2003;30(5):901-11.

Gray et al., Dual-mode laparoscopic fluorescence image-guided surgery using a single camera. Biomed Opt Express. Aug. 1, 2012;3(8):1880-90. doi: 10.1364/BOE.3.001880. Epub Jul. 17, 2012.

Hart et al., Cell binding and internalization by filamentous phage displaying a cyclic Arg-Gly-Asp-containing peptide. J Biol Chem. Apr. 29, 1994;269(17):12468-74.

Holland et al., Chapter 4. Biodegradable polymers. In: Advances in Pharmaceutical Sciences. Ganderton et al., eds. vol. 6. 1992:101-164.

Holsinger et al., Use of the photonic band gap fiber assembly CO2 laser system in head and neck surgical oncology. Laryngoscope. Jul. 2006;116(7):1288-90.

Hsiung et al., Detection of colonic dysplasia in vivo using a targeted heptapeptide and confocal microendoscopy. Nat Med. Apr. 2008;14(4):454-8. doi: 10.1038/nm1692. Epub Mar. 16, 2008.

Kong et al., Comparative analysis of different laser systems to study cellular responses to DNA damage in mammalian cells. Nucleic Acids Res. May 2009;37(9):e68. doi: 10.1093/nar/gkp221. Epub Apr. 7, 2009.

Licha et al., Synthesis and characterization of cyanine dyes as contrast agents for near-infrared imaging. SPIE. 1996;2927:192-8.

Lin et al., Novel near-infrared cyanine fluorochromes: synthesis, properties, and bioconjugation. Bioconjug Chem. May-Jun. 2002;13(3):605-10.

(56) References Cited

OTHER PUBLICATIONS

Liu et al., Hands-free, wireless goggles for near-infrared fluorescence and real-time image-guided surgery. Surgery. May 2011;149(5):689-98. doi: 10.1016/j.surg.2011.02.007.

Mahmood et al., Near-infrared optical imaging of protease activity for tumor detection. Radiology. Dec. 1999;213(3):866-70.

Moats et al., A "Smart" Magnetic Resonance Imaging Agent That Reports on Specific Enzymatic Activity. Angew Chem Int Ed Engl. 1997;36(7):726-8.

Mullenix et al., Secondary operations are frequently required to complete the surgical phase of therapy in the era of breast conservation and sentinel lymph node biopsy. Am J Surg. May 2004;187(5):643-6.

Negrin et al., In vivo-in vitro study of biodegradable methadone delivery systems. Biomaterials. Mar. 2001;22(6):563-70.

Palen et al., Substrate specificity of a hypothalamic neurosecretory granule enzyme capable of processing pro-gonadotropin releasing hormone precursor protein. Peptides. Jan.-Feb. 1987;8(1):21-4. Abstract only.

Poul et al., Selection of tumor-specific internalizing human antibodies from phage libraries. J Mol Biol. Sep. 1, 2000;301(5):1149-61.

Railton et al., Myocardial scintigraphy with I-123 heptadecanoic acid as a test for coronary heart disease. Eur J Nucl Med. 1987;13(2):63-6.

Ramanujam et al., Fast and noninvasive fluorescence imaging of biological tissues in vivo using a flying-spot scanner. IEEE Trans Biomed Eng. Sep. 2001;48(9):1034-41.

Reinisch, Laser physics and tissue interactions. Otolaryngol Clin North Am. Dec. 1996;29(6):893-914.

Rogakou et al., Megabase chromatin domains involved in DNA double-strand breaks in vivo. J Cell Biol. Sep. 6, 1999;146(5):905-16.

Singletary et al., Revision of the American Joint Committee on Cancer staging system for breast cancer. J Clin Oncol. Sep. 1, 2002;20(17):3628-36.

Tung et al., In vivo imaging of proteolytic enzyme activity using a novel molecular reporter. Cancer Res. Sep. 1, 2000;60(17):4953-8.

Tyagi et al., Multicolor molecular beacons for allele discrimination. Nat Biotechnol. Jan. 1998;16(1):49-53.

Vaidya et al., Intraoperative T staging in radical retropubic prostatectomy: is it reliable? Urology. May 2001;57(5):949-54.

Van Eenige et al., Clinical value of studies with radioiodinated heptadecanoic acid in patients with coronary artery disease. Eur Heart J. Mar. 1990;11(3):258-68.

Vogel et al., Mechanisms of pulsed laser ablation of biological tissues. Chem Rev. Feb. 2003;103(2):577-644.

Weissleder et al., In vivo imaging of tumors with protease-activated near-infrared fluorescent probes. Nat Biotechnol. Apr. 1999;17(4):375-8.

Weissleder et al., In vivo magnetic resonance imaging of transgene expression. Nat Med. Mar. 2000;6(3):351-4.

Yang et al., Presentation, 2010 IVIS Imaging System from Caliper LifeSciences, 104 slide presentation 52 pages.

Zaheer et al., In vivo near-infrared fluorescence imaging of osteoblastic activity. Nat Biotechnol. Dec. 2001;19(12):1148-54.

Zornig et al., Re-excision of soft tissue sarcoma after inadequate initial operation. Br J Surg. Feb. 1995;82(2):278-9.

Bach et al., Elevated lysosomal pH in Mucolipidosis type IV cells. Clin Chim Acta. Feb. 1999;280(1-2):173-9.

* cited by examiner

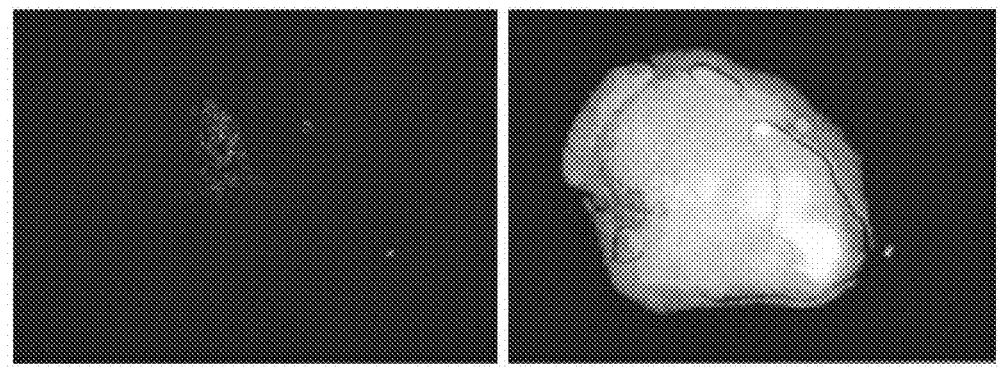
Figure 4
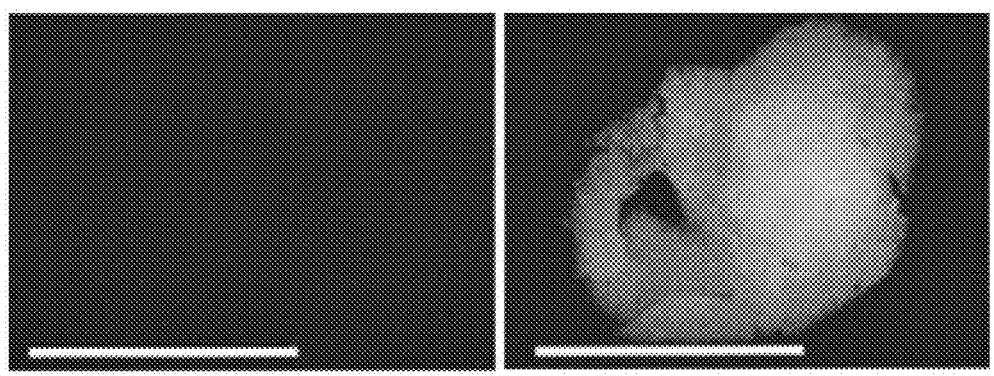
Figure 5
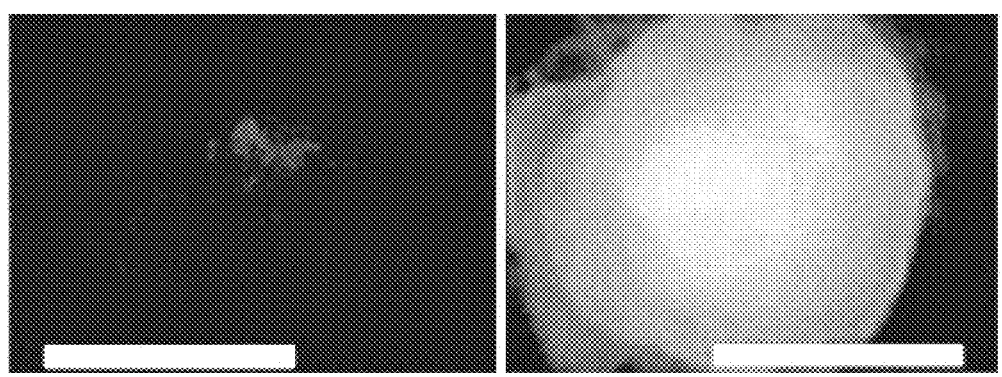
Figure 6A                    Figure 6B

IMAGING AGENT FOR DETECTION OF DISEASED CELLS

RELATED APPLICATIONS

This application claims priority under 35 U.S.C. §119(e) to U.S. Provisional Application Ser. No. 61/781,601, entitled "IMAGING AGENT FOR DETECTION OF DISEASED CELLS" filed on Mar. 14, 2013 and U.S. Provisional Application Ser. No. 61/785,136, entitled "IMAGING AGENT FOR DETECTION OF DISEASED CELLS" filed on Mar. 14, 2013, which are herein incorporated by reference in their entirety.

BACKGROUND OF THE INVENTION

There are over one million cancer surgeries per year performed in the United States and nearly 40% of them miss resecting the entire tumor according to the National Cancer Institute Surveillance Epidemiology and End Results report. For example in breast cancer lumpectomies, failure to remove all the cancer cells during the primary surgery (positive margins) occurs approximately 50% of the time and requires second surgeries. Residual cancer in the tumor bed is a leading risk factor for local tumor recurrence, reduced survival rates and increased likelihood of metastases. In addition, final histopathology of the resected tumor misses 25% of the residual cancer left in the tumor bed, which must be addressed with adjuvant medical therapy (e.g. radiotherapy or chemotherapy). This poor performance of pathology is primarily due to a sampling error since only a small fraction of the entire tumor is analyzed.

In a typical solid tumor resection, the surgeon removes the bulk of the tumor and sends it to pathology. The pathologist then samples the bulk tumor in a few locations and image a stained section under microscope to determine if the surgeon has completely removed all of cancer cells from the patient. Should the pathologist find a portion of the stained sample without normal cells bordering the cancerous cells (a diagnostic known in the medical realm as "positive margin"), the surgeon may be instructed to resect more tissue. However this pathology exercise is a time intensive procedure and often takes days for final results to be sent to the physician. Should a pathology report requiring additional resection return after the patient has completed the initial surgery, this may require the surgeon to perform a second surgery.

The current pathology process is not favored for a number of reasons. First, the pathology process relies on sampling a given tumor at certain spatial intervals which may result in missing a critical portion of the tumor and is therefore not a very reliable source of information. In addition, the process disrupts the surgical workflow since the physician and the patient have to wait for the pathology report to return prior to finishing the surgery or return for a second surgery should the pathology process exceed the time window for the first surgery. Leftover cancerous cells in a patient could result in cancer recurrence or additional necessary therapy (e.g. radiation, chemotherapy, etc.). There is a need for a system that improves upon the inefficiencies of the pathology process, reducing second surgeries, cancer recurrence, and additional medical therapy for cancer patients.

U.S. Patent Application publication number 20110104071 describes a system for detecting molecular imaging probes at or near the surface of exposed tissue during surgery, without confocal microscopy and related limitations on the field of view and depth of focus. The system can be used in clinical settings to guide surgery or therapy when localization of the target is important for treatment, such as for example in cancer treatment. The present invention is an improvement in that system, including, but not limited to, an improvement in the molecular imaging probe employed to detect target cells.

SUMMARY OF THE INVENTION

It has now been found that compounds of formula I, pharmaceutically acceptable salts thereof, and compositions thereof, are useful as imaging agents and exhibit desirable characteristics for the same. In certain embodiments, the present invention provides a compound of formula I,

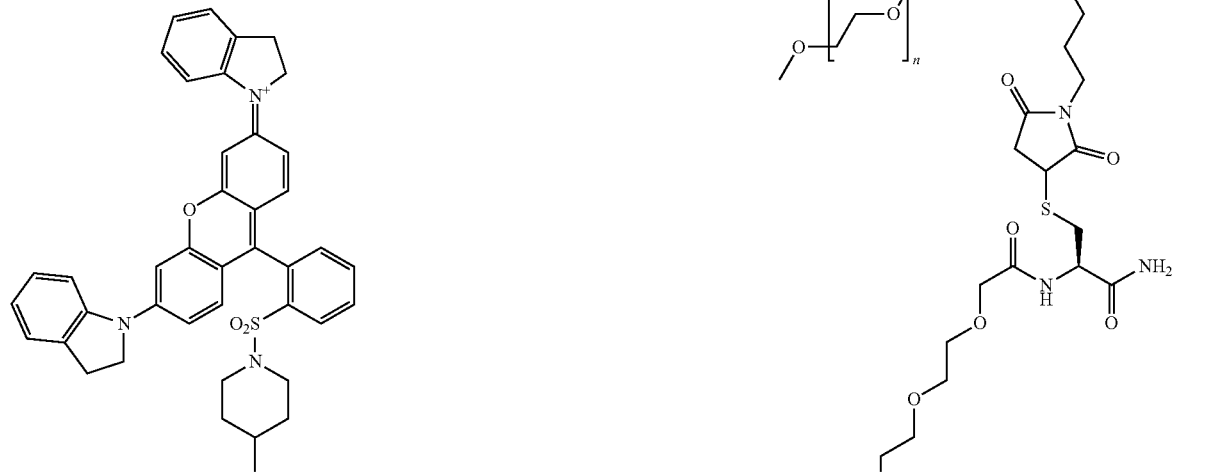

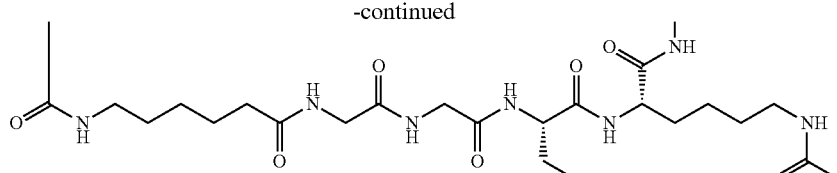

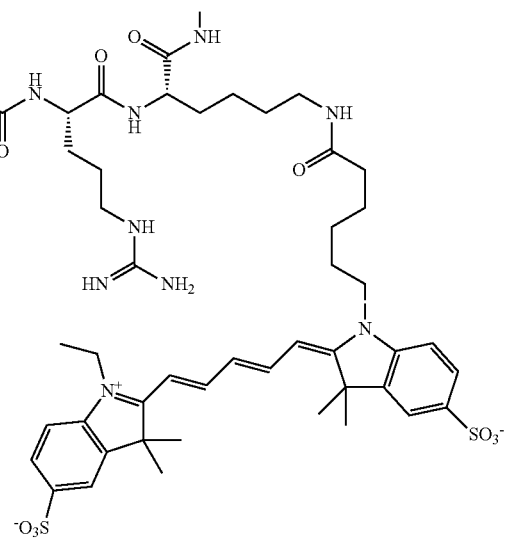

or a pharmaceutically acceptable salt thereof, wherein n is an integer between 400 and 500, inclusive. In certain embodiments, the present invention provides a compound of formula I, or a pharmaceutically acceptable salt thereof, wherein n is an integer between 440-460, inclusive. In certain embodiments, the present invention provides a compound of formula I, or a pharmaceutically acceptable salt thereof, wherein n is about 450. In certain embodiments, the present invention provides a compound of formula I, or a pharmaceutically acceptable salt thereof, wherein the mPEG portion of the molecule is about 20,000 g/mol in molecular weight. In certain embodiments, a compound of formula I is provided as an acetate salt. In certain embodiments, the present invention provides a pharmaceutical composition comprising a compound of formula I, or a pharmaceutically acceptable salt thereof.

In another aspect of the invention, provided herein is a composition comprising a plurality of compounds of formula I, or pharmaceutically acceptable salts thereof. In certain embodiments, the average value of n for the compounds in the composition is between 400-500, inclusive. In certain embodiments, the average value of n for the compounds in the composition is between 440-460, inclusive. In certain embodiments, the average value of n for the compounds in the composition is about 450. In certain embodiments, the average molecular weight of the mPEG portion of the molecules is about 20,000 g/mol.

In some embodiments, a compound of formula II, or a salt thereof, is provided:

II

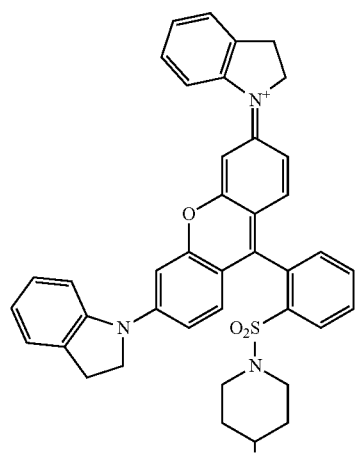

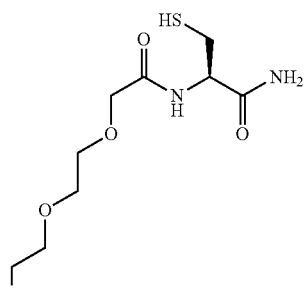

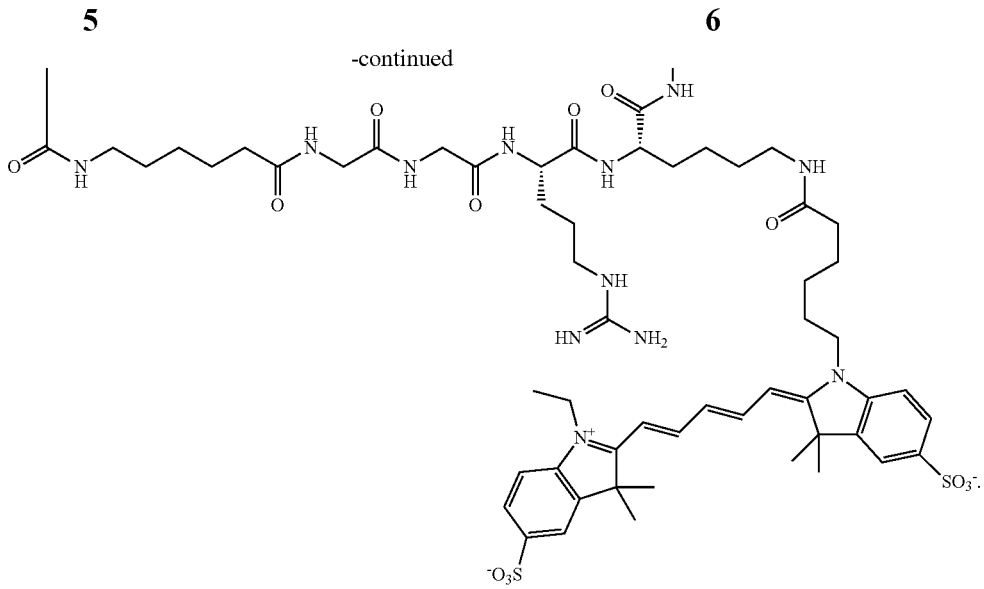

A compound of formula II is useful in the synthesis of compounds of formula I.

In certain embodiments, provided herein is an in-vivo method for spatially determining tissue heterogeneity of tissue of a subject comprising administering a composition provided herein to the subject; and obtaining after said administration step an in-situ image of said tissue. In certain embodiments, an in-vivo method described herein employs an imaging system having pixels with a field of view, and wherein the field of view of each pixel when said image is obtained is 4 cells or less, 3 cells or less, 2 cells or less, 1 cell or less, or less than 1 cell (e.g., 2, or 3, or 4, or more than 4 pixels per cell). In certain embodiments, the field of view of each pixel when said image is obtained is one cell or less than one cell. In certain embodiments, an image obtained using a provided imaging agent distinguishes between diseased cells and healthy cells within 5 mm, 4 mm, 3 mm, 2 mm, or even 1 mm from the surface of the tissue (including cells at the surface of the tissue). In certain embodiments, an image obtained using a provided imaging agent does not distinguish diseased cells and healthy cells that are deeper than 5 mm, 6 mm, 7 mm, 8 mm, 9 mm, or 10 mm from the surface of the tissue. In some embodiments, the tissue imaged using a provided method is the exposed tissue bed left behind after tumor resection.

BRIEF DESCRIPTION OF THE DRAWINGS

FIG. 4 depicts imaging with the LUM Imaging Device after injection of composition A into a dog with a mammary gland carcinoma 16 hours prior to surgery, wherein clear fluorescence contrast between normal fatty tissue (left) and tumor (right) from a mammary gland carcinoma may be observed. Scale bar: 5 mm.

FIG. 5 shows images obtained from a dog with an osteosarcoma in the left side of the chest wall. Images from fatty tissue (left) and the tumor mass (right) show distinct fluorescence emission. Scale bar: 5 mm.

FIG. 6 shows representative images of (a) resected healthy muscle and (b) sarcoma from a mouse 6 hours after injection with composition A. Scale bar: 5 mm.

DETAILED DESCRIPTION OF CERTAIN EMBODIMENTS

Figure 1:
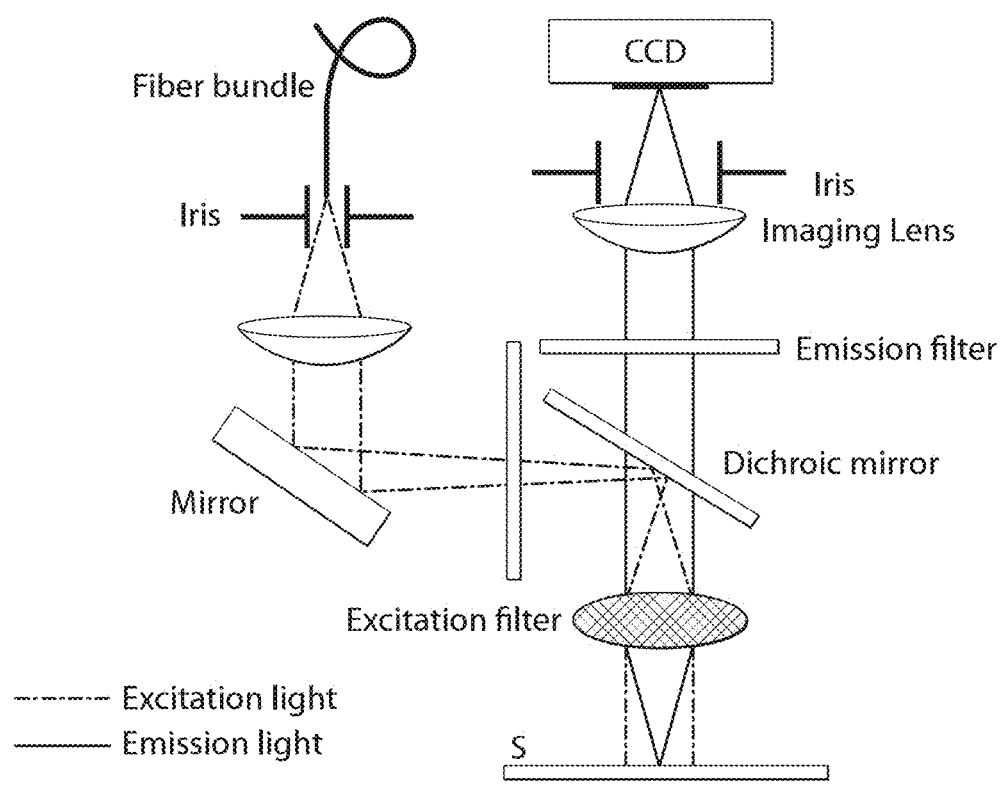
FIG. 1 shows an optical schematic of a prototype of a LUM Imaging Device.

Real-time detection of cancer cells during surgical tumor resection is a critical unmet need. Imaging agents described herein have characteristics that distinguish them from other imaging technologies. For instance, most optical imaging agents are aimed at near-infrared wavelengths above 700 nm to ensure that the detection is deep in the body. However, the technology provided herein is directed at diseased cells (e.g., residual cancer cells in the tumor bed) at or near the surface, and deep tissue detection is not the goal.

The following references describe methods of imaging, but do not disclose the Compounds of the present invention: A Novel Imaging System Permits Real-time in Vivo Tumor Bed Assessment After Resection of Naturally Occurring Sarcomas in Dogs, Clinical Orthopaedics and Related Research, September 2012 Volume 471:3, 834-842. William C. Eward D V M, MD, Jeffrey K. Mito M D, PhD, Cindy A. Eward D V M, Jessica E. Carter, Jorge M. Ferrer PhD, David G. Kirsch M D, PhD, Brian E. Brigman M D, PhD; Intraoperative detection and removal of microscopic residual sarcoma using wide-field imaging. Cancer. 2012 Nov. 1; 118(21):5320-30. doi: 10.1002/cncr.27458. Epub 2012 Mar. 21. Mito J K, Ferrer J M, Brigman B E, Lee C L, Dodd R D, Eward W C, Marshall L F, Cuneo K C, Carter J E, Ramasunder S, Kim Y, Lee W D, Griffith L G, Bawendi M G, Kirsch D G.

Provided herein are cathepsin-activatable imaging agents comprising a dark quencher (QSY21), an amino acid backbone, a fluorophore (Cy5), 6-aminohexanoic acid and aminoethoxyethoxyacetyl spacers, and a methoxypolyethylene glycol (mPEG) chain. In some embodiments, a provided compound does not emit fluorescence as the dark quencher absorbs emitted fluorescence from the fluorophore. Once cathepsins cleave a provided compound at the amino acid backbone, the Cy5 fluorophore emits detectable fluorescence. This technology is applicable to cancers at various anatomical sites (e.g., sarcoma and breast cancer) because the compound is activated by the family of cathepsin enzymes, which are upregulated in many types of cancer. Accordingly, such imaging agents distinguish cells which express more cathepsin and therefore cleave more of the cathepsin-activatable imaging agent from other cells which express lower levels of cathepsins or no cathepsins at all. A provided imaging agent is able to be administered to a subject (e.g., systemically), be taken up by a diseased cell in a tissue of interest (e.g., a tumor bed from a resected tumor), and be cleaved by a cathepsin in order to allow for detection of the cell by imaging. While cathepsin-activatable imaging agents have previously been described, imaging agents with the improved properties described herein are unpredictable over the general teachings in the art.

In certain embodiments, a provided compound is of formula I:

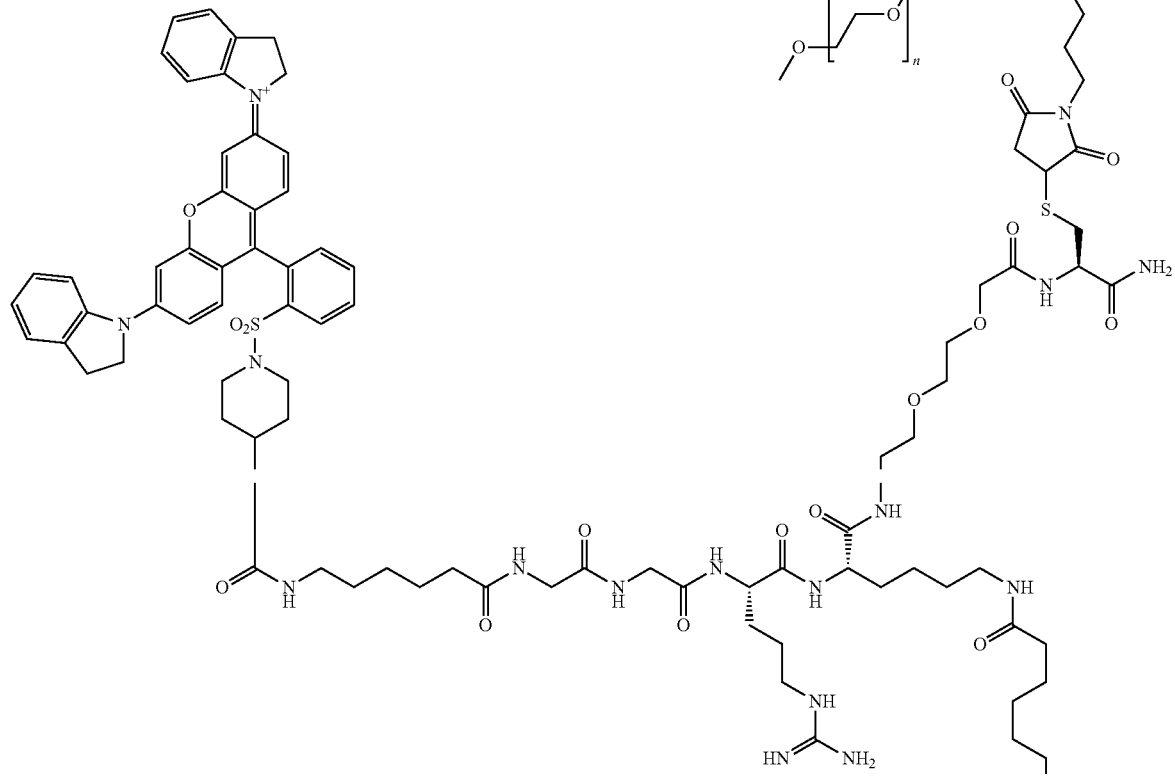

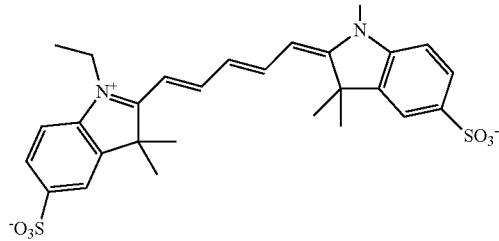

or a pharmaceutically acceptable salt thereof, wherein n is an integer between 400 and 500, inclusive. In some embodiments, n is an integer between 440-460, inclusive.

In formula I, all chiral amino acids are depicted as being in the L-configuration. While the L-configuration is important at or near an enzyme cleavage site, it will be understood that the cysteine residue which is remote from the cleavage site could, in certain embodiments, be present in the D-configuration. In some embodiments, a provided compound is compound 1:

I

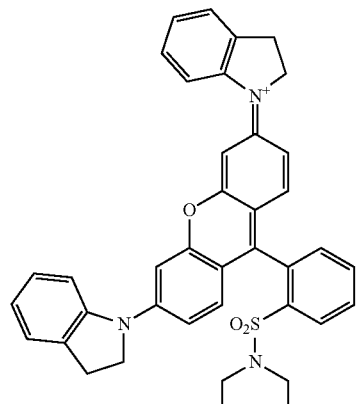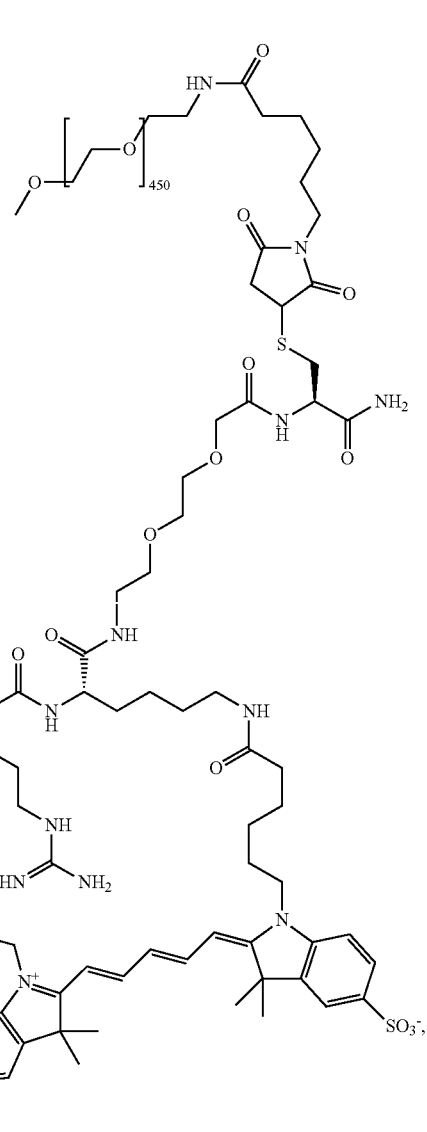

or a pharmaceutically acceptable salt thereof.

In certain embodiments, a compound of formula I is provided wherein the mPEG portion of the molecule (e.g., (e.g., 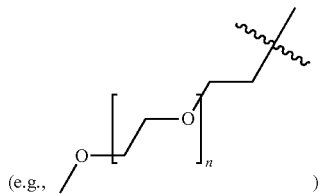 )

is about 20,000 g/mol in molecular weight± about 10%. In certain embodiments, a compound of formula I is provided wherein the mPEG portion of the molecule (e.g., (e.g., 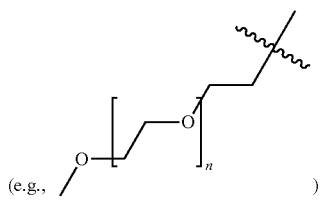 )

is about 20,000 g/mol in molecular weight± about 10%, with a polydispersity of ≤1.04.

In contrast to self-quenched imaging agents where two identical fluorophores in close proximity quench each other's fluorescence, compounds of formula I employ a combination of a fluorophore (Cy5) and a dark quencher (QSY21) to better suppress the fluorescence emission of the uncleaved form of the imaging agent. Because dark quenchers are more efficient in absorbing and dissipating the energy than self-quenchers, this approach reduces the level of background fluorescence. The fluorophore and dark quencher are separated by an aminohexanoic acid spacer and an amino acid sequence. The amino acid sequence is a substrate for cathepsin enzymes (Cat B, K, L, S), which are known to be overexpressed in many tumor types. Once cathepsins cleave a provided compound at the amino acid backbone, the Cy5 fluorophore emits detectable fluorescence. To influence the pharmacokinetics of the molecule, a ca. 20 kD mPEG chain is conjugated to a cysteine residue proximal to the fluorescent molecule. The aminoethoxyethoxyacetyl spacer provides separation between the cleavage site and the larger mPEG chain to improve access to the peptide substrate by the enzymes.

In some embodiments, a compound of formula I is provided as a salt. In some embodiments, a compound of formula I (e.g., compound 1) is provided as an acetate salt.

The phrase "pharmaceutically acceptable salt," as used herein, refers to pharmaceutically acceptable organic or inorganic salts of a provided compound. For use in medicine, the salts of the provided compounds will be pharmaceutically acceptable salts. Other salts may, however, be useful in the preparation of provided compounds or of their pharmaceutically acceptable salts. Pharmaceutically acceptable salts are well known in the art. For example, Berge et al., describe pharmaceutically acceptable salts in detail in *J. Pharm. Sci.* (1977) 66:1-19, incorporated herein by reference in its entirety. A pharmaceutically acceptable salt involves the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. When multiple charged atoms are present in the parent drug, its pharmaceutically acceptable salts will have multiple counter ions and there can be several instances of the same counter ion or different counter ions. Hence, a pharmaceutically acceptable salt can have one or more charged atoms in the parent compound and/or one or more counter ions.

Pharmaceutically acceptable salts of the compounds described herein include those derived from suitable inorganic and organic acids and bases. In some embodiments, the salts can be prepared in situ during the final isolation and purification of the compounds. In other embodiments the salts can be prepared from the free form of the compound in a separate synthetic step.

When a provided compound is acidic or contains a sufficiently acidic bioisostere, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. Quaternary ammonium salts such as $N^+(C_{1-4}\text{ alkyl})_4$ are also included.

When a provided compound is basic or contains a sufficiently basic bioisostere, salts may be prepared from pharmaceutically acceptable non-toxic acids, including inorganic and organic acids. Such acids include, but are not limited to, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, carbonic, boric, sulfamic, propionic, butyric, hydroxymaleic, mucic, phenylacetic, sulfanilic, aspartic, edetic, stearic, palmitic, oleic, lauric, ascorbic, valeric, perchloric, malonic, p-toluenesulfonic acid and the like. Particular embodiments include citric, hydrobromic, hydrochloric, maleic, phosphoric, sulfuric and tartaric acids. Other exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, palmoate (i.e., 1,1'-methylene-bis-(2-hydroxy-3-naphthoate)), adipate, alginate, ascorbate, aspartate, cyclopentanepropionate, borate, butyrate, camphorate, digluconate, dodecylsulfate, ethanesulfonate, glucoheptonate, glycerophosphate, hemisulfate, heptanoate, hexanoate, 2-hydroxyethanesulfonate, lactobionate, laurate, lauryl sulphate, malonate, 2-naphthalenesulfonate, nicotinate, pectinate, persulfate, 3-phenylpropionate, picrate, pivalate, propionate, stearate, thiocyanate, undecanoate, and valerate salts.

The preparation of the pharmaceutically acceptable salts described above and other typical pharmaceutically acceptable salts is more fully described by Berge et al., "Pharmaceutical Salts," *J. Pharm. Sci.*, 1977:66:1-19.

In some embodiments, a composition comprising a plurality of compounds of formula I is provided. In some embodiments, such a composition arises from the synthesis of a compound of formula I from a compound of formula II, wherein a compound of formula II is coupled with mPEG (20,000) aminohexylmaleimide, wherein the mPEG portion of the molecule is provided as a plurality of compounds with an average molecular weight of about 20,000 g/mol. One of ordinary skill in the art will understand that an mPEG polymer is provided as a heterogeneous mixture of molecular weights, and thus compositions prepared from an mPEG polymer will also be heterogeneous. In some embodiments, such a composition arises from the synthesis of a compound of formula I from a compound of formula II, wherein a compound of formula II is coupled with mPEG (20,000) aminohexylmaleimide, wherein the mPEG portion of the molecule is provided as a plurality of compounds with an average molecular weight of about 20,000 g/mol±10%. In some embodiments, such a composition arises from the synthesis of a compound of formula I from a compound of formula II, wherein a compound of formula II (shown below) is coupled with mPEG (20,000) aminohexylmaleimide, wherein the mPEG portion of the molecule is provided as a plurality of compounds with an average molecular weight of about 20,000 g/mol±10% with a polydispersity of ≤1.04.

II

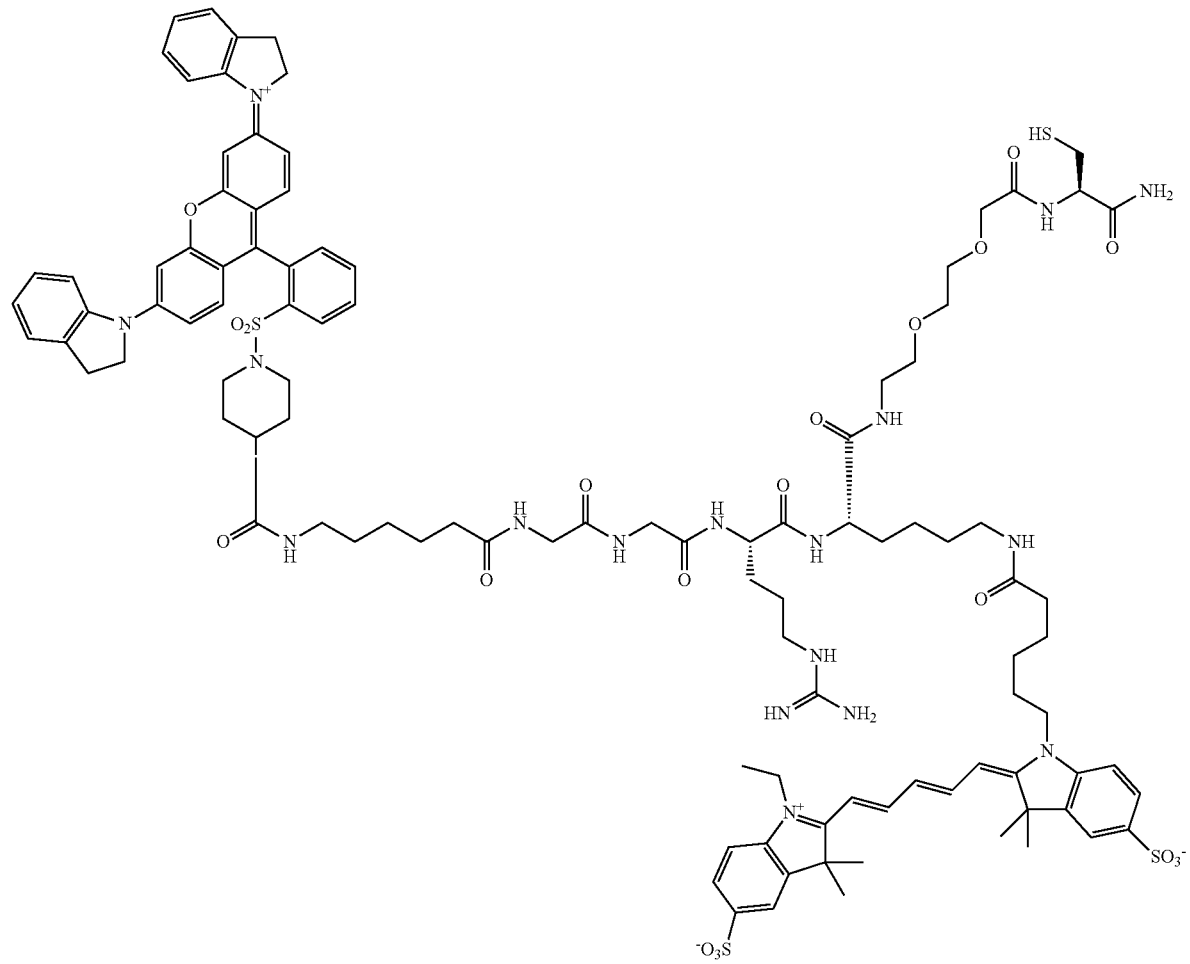

In certain embodiments, a composition comprising a plurality of compounds of formula I wherein the average value of n in the composition is in the range of 440-460 is provided. One of ordinary skill in the art will understand that the "average value of n" means that the majority of compounds in the composition fall within that range and the average value of those compounds falls within the range. In certain embodiments, a composition comprising a plurality of compounds of formula I wherein the average value of n in the composition is about 450 is provided. In certain embodiments, a composition comprising a plurality of compounds of formula I wherein the average molecular weight of the mPEG portion of the molecules (e.g.,

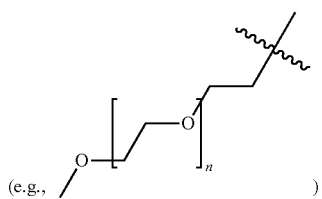

is about 20,000 g/mol±10% is provided.

In some embodiments, a compound of formula II, or a salt thereof, is provided. In some embodiments, the product of coupling a compound of formula II with mPEG (20,000) aminohexylmaleimide, wherein the mPEG portion of the molecule is provided as a plurality of compounds with an average molecular weight of about 20,000 g/mol, is provided. In some embodiments, the product of coupling a compound of formula II with mPEG (20,000) aminohexylmaleimide, wherein the mPEG portion of the molecule is provided as a plurality of compounds with an average molecular weight of about 20,000 g/mol±10%, is provided. In some embodiments, the product of coupling a compound of formula II with mPEG (20,000) aminohexylmaleimide, wherein the mPEG portion of the molecule is provided as a plurality of compounds with an average molecular weight of about 20,000 g/mol±10% with a polydispersity of ≤1.04, is provided.

Pharmaceutical Compositions

In some embodiments, a pharmaceutical composition comprising a compound described herein, e.g., a compound of formula I, or a pharmaceutically acceptable salt thereof, as described herein, and optionally a pharmaceutically acceptable excipient is provided. It will be understood by one of ordinary skill in the art that the compounds described herein, or salts thereof, may be present in various forms, such as anhydrous, hydrates, solvates, or polymorphs. In certain embodiments, a provided composition comprises a composition comprising a plurality of compounds of formula I as described herein. In certain embodiments, a compound or composition described herein, or a pharmaceutically acceptable salt thereof, is provided in an effective amount in the pharmaceutical composition. In certain embodiments, the effective amount is an amount effective for imaging a diseased cell (e.g., a cancer cell).

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Relative amounts of the imaging agent, the pharmaceutically acceptable excipient, and/or any additional ingredients in a pharmaceutical composition of the present disclosure will vary, depending upon the identity, size, and/or condition of the subject treated and further depending upon the route by which the composition is to be administered.

In some embodiments, a composition described herein is provided as a lyophilized solid. Such a lyophilized solid may be reconstituted for delivery as a liquid dosage form. Lyophilization is the process of freeze-drying a composition to remove excess water. The process involves the sublimation of the frozen water, usually under reduced pressure conditions. The process of lyophilization is well known in the art.

Cryoprotectants (cryoprotective agents or compounds) are agents that protect chemical compounds from the deleterious effects of freezing that may accompany lyophilization. Exemplary cryoprotectants include carbohydrates such as the saccharide sucrose, sugar alcohols such as mannitol, surface active agents such as the Tweens, as well as glycerol and dimethylsulfoxide. In certain embodiments, a cryoprotectant used in a provided composition is mannitol.

In certain embodiments, a cryoprotectant is present in a provided composition in an amount sufficient to allow the composition to be lyophilized. In certain embodiments, a cryoprotectant is present in an amount of about 0.5% to about 90%, about 1% to about 50%, about 2% to about 25%, about 25% to about 50%, about 40% to about 50%, based on the total weight of the lyophilized solid.

In some embodiments, a provided composition comprises a buffering agent. Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof. In certain embodiments, a provided composition comprises potassium phosphate as a buffering agent.

In some embodiments, a compound of formula I (e.g., compound 1), or a pharmaceutically acceptable salt thereof, or composition comprising a plurality of such compounds or salts, is formulated with mannitol. In some embodiments, a compound of formula I (e.g., compound 1), or a pharmaceutically acceptable salt thereof, or composition comprising a plurality of such compounds or salts, is formulated with sodium phosphate. In some embodiments, a compound of formula I (e.g., compound 1), or a pharmaceutically acceptable salt thereof, or composition comprising such compounds or salts, is formulated with sodium phosphate monobasic. In some embodiments, a compound of formula I (e.g., compound 1), or a pharmaceutically acceptable salt thereof, or composition comprising a plurality of such compounds or salts, is formulated with sodium phosphate dibasic. In some embodiments, a compound of formula I (e.g., compound 1), or a pharmaceutically acceptable salt thereof, or composition comprising a plurality of such compounds or salts, is formulated with mannitol, sodium phosphate monobasic, or sodium phosphate dibasic, or a combination thereof. In some embodiments, a compound of formula I (e.g., compound 1), or a pharmaceutically acceptable salt thereof, or composition comprising a plurality of such compounds or salts, is formulated with mannitol, sodium phosphate monobasic, and sodium phosphate dibasic. In some embodiments, a composition is provided comprising a compound of formula I (e.g., compound 1), or a pharmaceutically acceptable salt thereof, or composition comprising a plurality of such compounds or salts, mannitol, sodium phosphate monobasic, and sodium phosphate dibasic.

In some embodiments, a compound of formula I, or pharmaceutically acceptable salt thereof, or composition comprising such compounds or salts, is stored as a lyophilized cake and is reconstituted (e.g., with sterile 0.45% saline) prior to injection. In some embodiments, the lyophilized cake further comprises a cryoprotectant (e.g., mannitol) and/or a buffering agent (e.g., sodium phosphate buffer, e.g., sodium phosphate dibasic and sodium phosphate monobasic).

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

It should be understood that the foregoing compositions of compounds of Formula I together with one or more of, or any and all combinations of, a cryoprotectant, a buffer, a solvent, a sterilizing agent, a preservative, and/or saline, are aspects of the invention.

Liquid dosage forms (e.g., for parenteral administration) include pharmaceutically acceptable emulsions, microemulsions, solutions, suspensions, syrups and elixirs. In addition to an imaging agent, a liquid dosage form may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. In certain embodiments for parenteral administration, the compounds described herein are mixed with solubilizing agents such as Cremophor™, alcohols, oils, modified oils, glycols, polysorbates, cyclodextrins, polymers, and mixtures thereof.

Dosage forms for topical administration of a provided compound may include ointments, pastes, creams, lotions, gels, powders, solutions, or sprays. Generally, the active ingredient is admixed under sterile conditions with a pharmaceutically acceptable carrier and/or any desired preservatives and/or buffers as can be required.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in unit dosage form for ease of administration and uniformity of dosage. It will be understood, however, that the total dosage of provided compositions will be decided by the attending physician within the scope of sound medical judgment. The specific effective dose level for any particular subject or organism will depend upon a variety of factors including the tissue being imaged; the specific composition employed; the age, body weight, general health, sex and diet of the subject; the time of administration, route of administration, and rate of excretion of the imaging agent employed; drugs used in combination or coincidental with the imaging agent employed; and like factors well known in the medical arts.

In certain embodiments, a typical dose ranges from about 0.01 mg/kg to about 1000 mg/kg, (e.g., from about 0.01 mg/kg to about 100 mg/kg, from about 0.1 mg/kg to about 100 mg/kg, from about 1 mg/kg to about 100 mg/kg, from about 1 mg/kg to about 10 mg/kg, from about 0.1 mg/kg to about 10 mg/kg, from about 0.1 mg/kg to about 1 mg/kg). In certain embodiments, a dose ranges from about 0.25 mg/kg to about 1.5 mg/kg.

Methods

Imaging agents described herein can be used to assess tissues specifically for the detection of cancer cells during surgical excisions using intra-operative optical imaging. In certain embodiments, the sensitivity of the system allows for single cell detection. In certain embodiments, provided methods allow the assessment of cancer cells during surgical excision. In certain embodiments, methods using the imaging agents described herein allow cancer cells to be distinguished from normal cells allowing for complete resection of the tumor, leaving no residual cancer cells in the tumor bed. Such methods may allow for real time detection of residual cancer cells in the tumor bed during surgical resection. In certain embodiments, real time examination of the resected tumor allows for clean (or negative) margins in the tumor bed. By "clean margin," it is meant that there is an edge of normal tissue surrounding the resected tissue. In certain embodiments, the methods allow for examination of the resected tumor to determine whether the surface of the resected tissue is free of tumor cells.

Imaging agents described herein can be employed in methods previously described in U.S. Patent Application publication number 20110104071. In some embodiments, such methods employ an imaging device previously described in U.S. Patent Application publication number 20090299196. The disclosures of these published applications are incorporated herein by reference.

In certain embodiments, the device used in trials with mice is a lightweight hand-held tool with a small profile to allow maneuverability as well as to limit the intrusiveness of the device within the operating room. In certain embodiments, the device employs white light illumination to deliver excitation photons to the specimen and a combination of spectral filters for fluorescence excitation and collection. In certain embodiments, the image at the CCD plane has no magnification. In such embodiments, by maintaining a 1:1 ratio, individual cells can be detected because their fluorescence emission is mapped onto 1-4 pixels, improving the sensitivity and the signal-to-noise ratio of weak signals. In certain embodiments, the device has a wide field of view (e.g., 9 mm×6.4 mm). In certain embodiments, the imaging device is connected to a standard computer, which collects, analyzes, and displays the resulting image for the physician.

In certain embodiments, an in-vivo method for spatially determining tissue heterogeneity of tissue of a subject is provided comprising administering a pharmaceutical composition described herein to the subject; and obtaining after said administration step an in-situ image of said tissue. In certain embodiments, the image is obtained using an imaging system having pixels with a field of view, and wherein the field of view of each pixel when said image is obtained is one cell or less than one cell. In certain embodiments, the composition is administered systemically. In certain embodiments, the composition is administered systemically and the image is obtained between 12 and 72 hours (e.g., between 24 and 72 hours, or between 12 and 36 hours) after the composition is administered. In certain embodiments, the time between administration and imaging is one that allows for adequate cathepsin cleavage products of compounds of formula I to accumulate in diseased cells. In other embodiments, the composition is administered topically in vivo. In certain embodiments, the composition is administered topically in vivo and the image is obtained within 2 hours after the composition is administered. Imaging agents provided herein allow for selective viewing of cells at or near the surface (e.g., within about 1 cm from the surface, e.g., about 1 mm, about 2 mm, about 3 mm, about 4 mm, about 5 mm, about 6 mm, about 7 mm, about 8 mm, about 9 mm) of a tissue of interest. In certain embodiments, the image obtained distinguishes between diseased cells and healthy cells within about 1 cm from the surface, e.g., about 1 mm, about 2 mm, about 3 mm, about 4 mm, about 5 mm, about 6 mm, about 7 mm, about 8 mm, about 9 mm, from the surface of the tissue. In certain embodiments, the image obtained distinguishes between diseased cells and healthy cells within 5 mm, 4 mm, 3 mm, 2 mm, or even 1 mm from the surface of the tissue. In certain embodiments, the image obtained does not distinguish between diseased cells and healthy cells that are deeper than 1 cm from the surface of the tissue. In certain embodiments, the image obtained does not distinguish between diseased cells and healthy cells that are deeper than 5 mm, 6 mm, 7 mm, 8 mm, 9 mm, or 10 mm from the surface of the tissue. In certain embodiments, the tissue being imaged is the tissue bed left behind after tumor resection.

EXAMPLES

Imaging Agent

Composition A comprises compounds of formula I, which comprise a PEGylated heptapeptide covalently linked to both a fluorophore (Cy5) and a dark quencher (QSY21). The central heptapeptide provides both cathepsin substrate specificity and proper spacing of the fluorophore and quencher. The QSY21 and Cy5 functionalities are covalently attached to the α-amino terminus of the peptide and to the ε-amino group of lysine, respectively. An aminoethoxyethoxyacetyl group is incorporated into the amide backbone and the carboxy terminus of the heptapeptide is further modified by attachment of a 20 kDa methoxypolyethylene glycol (mPEG) molecule to the side chain of cysteine.

In certain embodiments, composition A is supplied lyophilized, in bulk powder form as an acetate salt. The 20 kDa methoxy-polyethylene glycol moiety has a variable molecule weight of 10%. One of ordinary skill in the art will understand that composition A comprises multiple compounds that vary in the molecular weight of the mPEG portion of the molecule, and the average molecular weight of the mPEG portion of the compounds in composition A is about 20 kDa. Accordingly, the average molecular weight of the compounds of formula I in the composition is about 22,078 g/mol. Composition A is dark blue in color due to the presence of both the dark quencher (QSY21) and the fluorophore.

Composition A acetate was produced using solid phase Fmoc (9-fluorenylmethoxycarbonyl) synthesis methods. Upon completion of the manufacturing process, identity of the bulk product was established by MALDI-TOF mass spectral analysis. The synthetic process used for manufacture of composition A acetate involved the following main steps: 1) solid phase synthesis of the protected peptide; 2) solid phase dye (Cy5 and QSY21) conjugation; 3) trifluoroacetic acid (TFA) cleavage; 4) purification of crude dye-conjugated peptide; 5) mPEG conjugation; 6) purification of mPEGylated peptide; 7) bulk API isolation.

The peptide synthesis was carried out at room temperature in a glass vessel comprising a fritted disk of coarse porosity.

The reaction vessel is equipped with a mechanical stirrer to allow for efficient mixing of the peptide-resin. Ramage (tricyclic amide linker) resin, a co-polymer that consists of 1% cross-inked polystyrene-divinylbenzene beads (200-400 mesh), was used for the synthesis.

The combination of protecting groups chosen for the synthesis of composition A acetate is commonly used in solid phase peptide syntheses. In solid phase synthesis, the reactive functional groups of the amino acids are selectively protected to avoid undesirable side reactions. The protecting groups are of two natures: base-labile and acid-labile. A 9-fluorenylmethoxycarbonyl (Fmoc) functionality is used as the base-labile, α-amino protecting group. The Fmoc group prevents undesirable side reactions of the α-amino group during the coupling reaction, and is later removed to allow the introduction of the next amino acid in the sequence. The side chains of the amino acids are selectively protected with protecting groups which are resistant to the deblocking mixtures (20% piperidine in dimethylformamide (DMF), v/v). The side protecting groups utilized were phenyl-methyl (Trt) for cysteine, 1-(4,4-dimethyl-2,6-dioxocyclohex-1-ylidene)-3-methylbutyl (ivDde) for lysine, and 2,2,4,6,7-pentamethyldihydrobenzo-furane (Pbf) for arginine. Following the peptide synthesis and dye conjugation steps, the Trt and Pbf groups were removed using a solution of a strong acid (92.5% trifluoroacetic acid (TFA)) and carbonium ion scavengers (triisopropylsilane (TIPS), ethanedithiol (EDT), $H_2O$). The following amino acids were used in the synthesis of composition A: Fmoc-AEEAc-OH; Fmoc-Arg(Pbf)-OH; Fmoc-ε-Ahx-OH; Fmoc-Cys(Trt)-OH; Fmoc-Gly-OH; Fmoc-Lys(ivDde)-OH. All are available from Bachem (catalog numbers B-3635, B-2375, B-1560, B-1440, B-1330, and B-3515, respectively).

General Manufacturing Process.

Cleavage of the Fmoc protecting group on Ramage resin was performed with 20% piperidine in DMF, an Fmoc-protected amino acid was coupled, and the Fmoc cleavage and amino acid coupling steps were repeated for 6 cycles. Cleavage of the ivDde protecting group on the resin-bound peptide was followed by conjugation of Cy5-NHS dye. Cleavage of the Fmoc protecting group on the resin-bound peptide was followed by conjugation of QSY21-NHS dye. Acid-labile side chain protection groups were cleaved, followed by cleavage of peptide from resin with TFA/TIPS/EDT/$H_2O$ and precipitation of peptide with isopropyl ethyl (IPE). The crude dye-conjugated peptide was purified and subject to in-process lyophilization. mPEG (20,000) amino-hexylmaleimide was conjugated to the purified dye-conjugated peptide, then further purified and subject to in-process lyophilization. The purified mPEGylated dye-conjugated peptide was reconstituted and lyophilized to give composition A acetate.

Peptide Synthesis.

Deprotection: During the deprotection step, the base-labile protecting group (Fmoc) was cleaved from the α-amino function of the N-terminal amino acid on the growing peptide chain by treating the resin twice with a 20% mixture of piperidine in DMF. Wash cycle: The wash steps were performed in eliminate excess reagents used in the preceding step. The solvents selected for each step are chosen to insure that there is no risk of introducing an undesirable side reaction while eliminating the excess of reagents as efficiently as possible. The duration of each wash step is timed to allow for thorough contact of the peptide-resin with the solvent and to provide ample time for extraction of the reagents. DMF is used after deprotection as well as after coupling because it has excellent solubilizing properties for all reagents used in the coupling step and for its resin-swelling properties. Conversely, isopropanol (IPA) is used due to its ability to shrink the resin, which also aids in removal of excess solvents. Activation and coupling: During the activation and coupling steps, the deprotected α-amino group is acylated by the next activated amino acid in the sequence. The reagents used to accomplish acylation were selected to create optimal reaction conditions and easy elimination of the excess reagents at the end of the coupling reaction. Activation of the amino acid derivative used for the first coupling, Fmoc-Cys(Trt)-OH, was performed by dissolving a 1.7-fold excess of the protected amino acid with coupling reagents OxymaPure and 1,3-diisopropylcarbodi-imide (DIC) in DMF. The solution of activated amino acid was then added to the peptide-resin. The suspension was stirred at room temperature for 20 minutes, after which a second aliquot of DIC was added to the reaction mixture. The mixture was stirred and allowed to react for one to three hours. Activation of the remaining amino acid derivatives was performed by dissolving a 1.7-fold excess of the protected amino acid with coupling reagents 1-H-benzotriazo-lium-1-[bis(dimethylamino)methylene]-5-chloro-tetrafluo-roborate(1-),3-oxide (TCTU) and diisopropylethylamine (DIPEA) in DMF. The suspension was stirred at room temperature for approximately 10 minutes, after which a second aliquot of DIPEA was added to the reaction mixture. The mixture was stirred and allowed to react for a minimum of one hour and maximum of three hours. Recoupling and acetylation: After a minimum reaction time of one hour, the presence of remaining unreacted amino groups was monitored using the qualitative TNBS (trinitrobenzenesulfonic acid) test and the ninhydrin test. The TNBS test was performed by adding a few drops of trinitrobenzenesulfonic acid to a sample of the peptide-resin in a test tube and allowing the two to react for three minutes. The presence of free amino groups causes a colored reaction. Orange-colored beads indicate incomplete coupling and presence of unreacted amine. Similarly, in the ninhydrin test, a few drops of the ninhydrin reagents are added to a sample of the peptide-resin in a small test tube. Blue-stained resin beads indicate the presence of unreacted amine. If some residual amino groups are detected by either of the above-mentioned tests, the coupling reaction is repeated using half the amount of amino acid derivative and coupling reagent required for the first coupling reaction. The TNBS and ninhydrin tests are performed each time recoupling takes place to visualize the presence of unreacted amino functions. Unreacted α-amino functions still present after recoupling were acetylated using acetic anhydride to avoid undesirable deletion sequences in the next cycle. After coupling of the last amino acid in the sequence was completed, the peptide-resin was thoroughly washed using IPA, dried and weighed. The yield of the peptide-resin at this stage may be used as an indication of the efficiency of the synthesis. For lot FLUM1101A, no acetylation reactions were required; the yield for the synthesis step was 89.6%.

Solid-Phase Dye Conjugation.

Cy5-NHS dye: The side chain protecting group (ivDde) on the lysine was removed by treating the dried peptide-resin with a mixture of imidazole and hydroxylamine hydrochloride that had been dissolved in DMF/dichloromethane (DCM). The mixture was allowed to stir for about 7 hours. The peptide resin was then washed alternately with DMF and IPA. Coupling of the Cy5-NHS dye (Cy5 mono NHS ester; available from GE, catalog no 28-9288-45) was performed by dissolving the dye in DMF and adding it to the reactor containing the peptide-resin. The mixture was stirred for 20 minutes after which N-methylmorpholine (NMM) was added. Stirring was then continued for a minimum of 2 hours. Completion of the dye conjugation was monitored by analytical HPLC. After conjugation, the reaction was drained, washed with IPA and DMF, and treated with a mixture of acetic anhydride and DIPEA in DMF to acetylate any remaining unreacted sites on the lysine side chain. QSY21-NHS dye: The Fmoc group was cleaved from the α-amino function of the N-terminal amino acid by treating the resin twice with a 20% mixture of piperidine in DMF, followed by washes using DMF and IPA. The QSY21-NHS dye (QSY carboxylic acid, succinimidyl ester; available from Invitrogen, catalog no Q26414) was dissolved in DMF and added to the reactor containing the peptide-resin. The mixture was stirred for 10-20 minutes after which N-methylmorpholine (NMM) was added. Stirring was then continued for a minimum of 2 hours. Completion of the dye conjugation was monitored by analytical HPLC. After conjugation, the reactor was drained, washed with DMF and IPA, and dried under vacuum. The yield for the solid phase dye conjugation step was 76.4%.

Cleavage and Deprotection.

During the cleavage operation, the dye-conjugated peptide was detached from the resin with concomitant cleavage of the acid-labile side chain protecting groups. This was accomplished by treatment of the peptide-resin with a cooled, strong acid (TFA) in the presence of scavengers. Triisopropylsilane (TIPS), ethanedithiol (EDT), and water act as scavengers and are used to provide a protonated cleavage environment which in turn gives higher quality crude product. Following the cleavage operation, the crude peptide was precipitated using cooled isopropyl ether (IPE), filtered using a fritted glass funnel and dried in a vacuum oven. After drying was completed, yield of the crude peptide is determined and recorded. The yield of the cleavage step for lot FLUM1101A was 75.1%.

Purification of the Dye-Conjugated Peptide.

The purification was performed by preparative HPLC. Equipment: The purification equipment was based on the principle of axial compression in which the chromatographic support is packed in a stainless steel compression module. A constant pressure was applied all along the column. The solvents were delivered through pumps and the necessary gradients were created with an automatic gradient maker. Nature of support: The purification of the crude dye-conjugated peptide was accomplished by preparative HPLC using reversed phase C18 material as the support. The C18 reversed phase material consists of a silica gel coated with C18 aliphatic chains; the free remaining silanol groups have been end-capped to avoid undesirable ionic interaction/binding between the mixture to be purified and the support. The separation is based on the hydrophobic interaction between the peptide and the support. Purification: A typical purification run comprised three steps: equilibration of the column to avoid elution of the product in the loading phase, loading and elution of the product, and washing of the column in preparation for the next run. Equilibration of the column was accomplished with aqueous trifluoroacetic acid (TFA). The crude dye-conjugated peptide was dissolved in an aqueous solution of 0.1% TFA and acetonitroile, and pumped onto the column. The product was eluted with aqueous TFA in a gradient of organic modifier (acetonitrile ($CH_3CN$)). After product elution, the column was washed with aqueous methanol (MeOH). The quality of the fractions that were collected as the peptide eluted from the column was monitored by analytical reversed phase HPLC. Fractions with purity ≥95% were pooled and lyophilized. Fractions with purity <95% and ≥70% were recycled through the same purification step. Fractions with purity <70% were discarded.

PEG Conjugation.

The purified dye-conjugated peptide was added to a solution of mPEG (20,000) aminohexylmaleimide (Vectra MPEG Epsilon Maleimide 20,000 Da, available from Bio Vectra Inc., catalog no 6266) that had been dissolved in aqueous sodium acetate (NaOAc) in ethylenediaminetetraacetic acid (EDTA). The solution was stirred for at least 3 hours. Completion of the PEG conjugation reaction was monitored by analytic HPLC.

Specifications of mPEG (20,000) aminohexylmaleimide.
Structure:

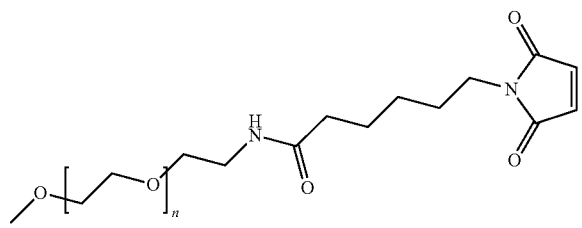

Molecular weight of mPEG portion of starting material is 20,000 Da±10%, and polydispersity is ≤1.04.

Purification of the PEGylated Dye-Conjugated Peptide.

The purification was performed by preparative HPLC. Equipment: The purification equipment was based on the principle of axial compression in which the chromatographic support is packed in a stainless steel compression module. A constant pressure was applied all along the column. The solvents were delivered through pumps and the necessary gradients were created with an automatic gradient maker. Nature of support: The purification of the PEGylated dye-conjugated peptide was accomplished by preparative HPLC using reversed phase support. The separation is based on the hydrophobic interaction between the peptide and the support. Purification: Equilibration of the column was accomplished by washing with aqueous acetic acid, followed by 0.1 M ammonium acetate ($NH_4OAc$). The PEGylated peptide solution was diluted with water, and pumped onto the column. Product elution was achieved using a gradient of aqueous acetic acid in acetonitrile. After product elution, the column was washed with aqueous methanol (MeOH). The quality of the fractions that were collected as the peptide eluted from the column was monitored by analytical reversed phase HPLC. Fractions with purity ≥95% were pooled and lyophilized. Fractions with purity <95% and ≥70% were recycled through the same purification step. Fractions with purity <70% were discarded. The yield for this purification step was 72.0%.

Reconstitution and Final Lyophilization.

Lyophilized pools resulting from the purification process with purity ≥95% were dissolved in an aqueous solution of acetic acid in Sterile Water for Irrigation USP, and combined to obtain a homogeneous solution. The solution was filtered through a 0.45-μM filter membrane cartridge and lyophilized to obtain the final bulk composition A acetate. The final overall yield for lot FLUM1101A was 9.0%.

Formulation of Composition A for Injection.

Composition A acetate was dissolved in sterile water, mannitol, and a sodium phosphate buffer, sterile filtered, and lyophilized. The target per unit vial was 10 mg composition A acetate, 10 mg mannitol, 0.84 mg sodium phosphate monobasic, and 0.43 mg sodium phosphate dibasic. The lyophilized solid can be reconstituted with 0.45% saline (e.g., about 0.1 mL to about 10 mL, about 0.5 mL to about 5 mL, about 0.5 to about 2 mL, about 1 mL).

LUM Imaging Device

A prototype LUM Imaging Device was used in veterinary settings with dogs, in laboratory settings with mice, and for in vitro assays. The LUM Imaging Device is a lightweight, hand-held tool with a small profile shown schematically in FIG. 1. The device employed white light illumination (300 W Xenon lamp) to deliver excitation photons to the specimen. This, in combination with specific spectral filters (excitation filter, dichroic mirror, and emission filter) allows for excitation (649 nm wavelength) of the Cy5 fluorophore on a compound of formula I (e.g., compound 1, e.g., composition A) and collection of its fluorescence emission (670 nm wavelength) once the compound has been cleaved. Several achromatic doublet lenses are used to relay the fluorescence image at no magnification into a commercial camera that utilizes a charge-coupled device (CCD). The CCD camera is connected to a desktop computer for image acquisition and display. Data acquisition software is written in C++. Image analysis is performed using MatLAB (Mathworks; Natick, Mass.) and ImageJ (National Institutes of Health). The device was built from standard parts from opto-mechanics vendors along with several custom-made components.

Figure 2:
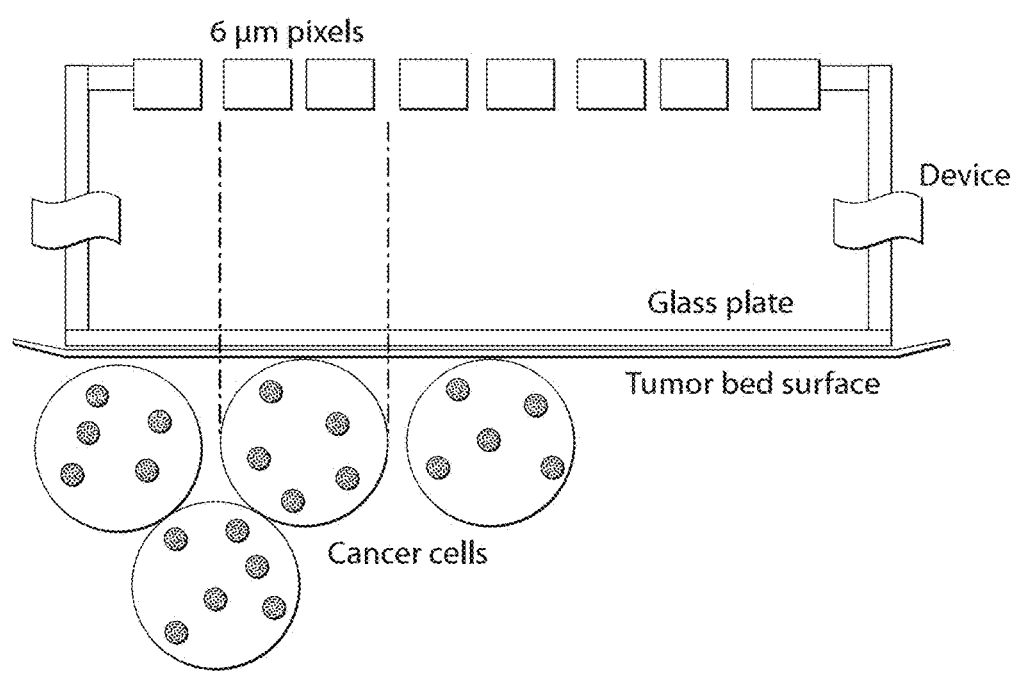
FIG. 2 shows a cross-section view of a simplified model of single cell detection (only a few camera pixels are shown for clarity). The LUM Imaging Device is placed over the tumor bed and a single cell is mapped onto 4 pixels (only two pixels shown in the plane) using a 1:1 lens system (not shown). Dark dots represent activated composition A by cathepsin enzymes inside cancer cells.

The LUM Imaging Device can identify a single cancer cell left behind anywhere in the tumor bed in milliseconds, guiding the surgeon to remove the area containing the residual cancer. The principle behind the imaging system is to map a single cancer cell (approximately 15 μm) onto 4 pixels (6 μm each) of the camera, resulting in single cell detection in a wide field of view (e.g. 5 cm) without magnification. This approach detects light emitted from a single cell but does not delineates the shape (morphology) of the cell, which is not necessary for cancer detection. FIG. 2 shows a schematic cross-section view of a simplified model of single cell detection (only a few camera pixels are shown for clarity). The LUM Imaging Device is placed over the tumor bed and a single cell is mapped onto 4 pixels (only two pixels shown in the plane) using a 1:1 lens system (not shown). Dark dots represent activated composition A by cathepsin enzymes inside cancer cells. The LUM Imaging device used in the experiments below was outfitted with a stainless steel, autoclavable spacer with a glass window which comes in contact with the specimen and keeps the device at the desired focal plane. This feature minimizes focal changes due to movements of the tissue and/or operator. The device had a field-of-view of 9 mm×6.4 mm, weighs 580 grams, and has dimensions of 229 mm×95 mm×50 mm.

To intraoperatively determine the level of fluorescence corresponding to cancerous tissue, images from the resected tissue are used to calibrate the system. A discrimination threshold is set based upon the lowest fluorescence intensity measured within the tumor image on a case-by-case basis.

The Lum Imaging Device presently used is the subject of patent application Ser. No. 14/211,201, filed on even date herewith, and entitled MEDICAL IMAGING DEVICE AND METHODS OF USE, the disclosure of which is incorporated herein by reference.

In general, the prototype Lum Imaging Device used in the examples below can be described as follows. The camera assembly is connected to a computer (Dell Optiflex 755, Intel Core Duo, 2.33 GHz, Windows XP, or similar) and a monitor (Samsung Model 2433BW, 1920×1200 pixels, 24 inches). The custom imaging acquisition software written in C++ is then installed on the computer.

Figure 3:
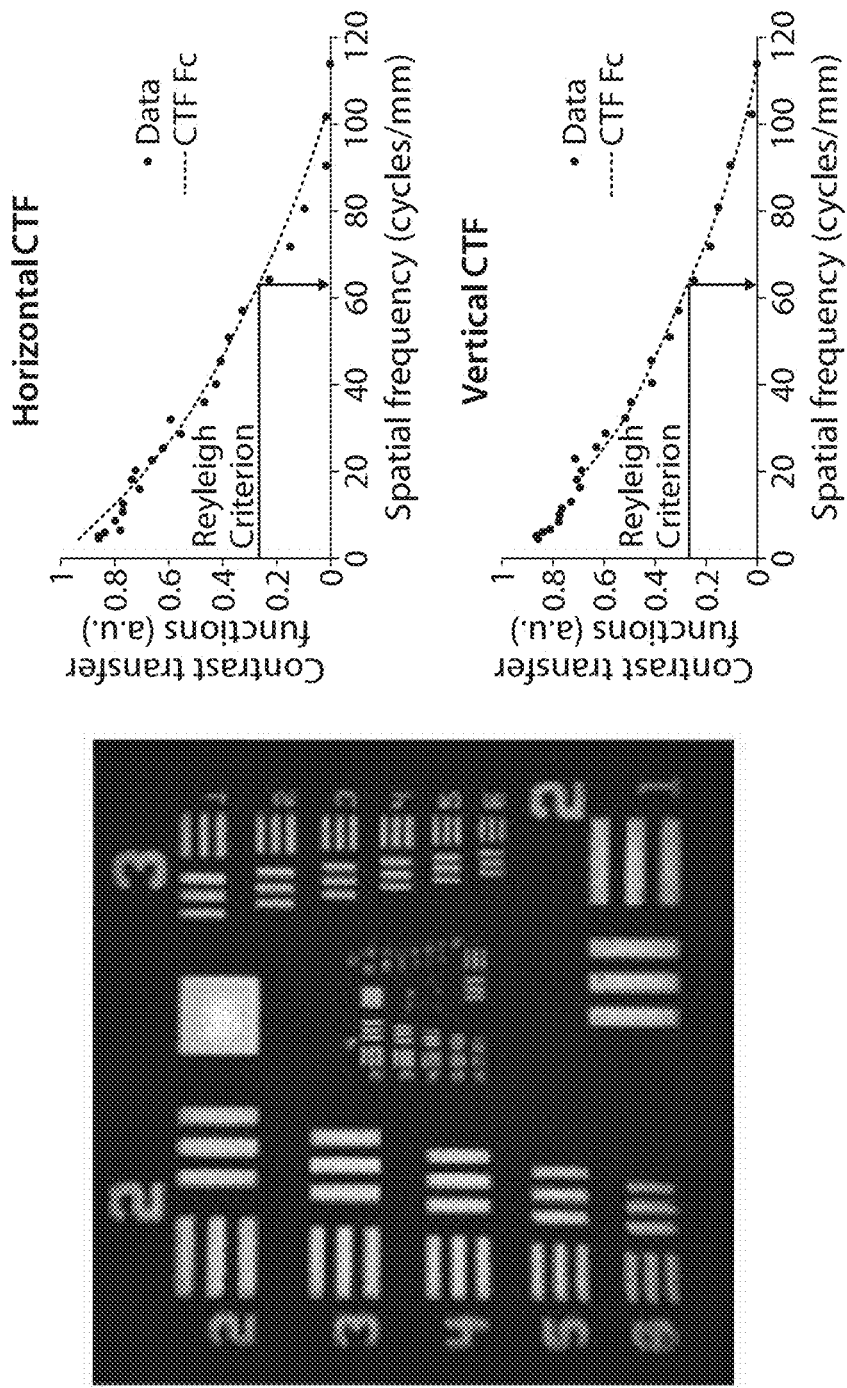
FIG. 3 shows an image of a standard U.S. Air Force 1951 resolution target (left) acquired with the LUM Imaging Device to determine the spatial resolution of the system and resultant horizontal and vertical (right) contrast transfer functions.

The computer, monitor, and light source are turned on at least 15 minutes prior to starting the data acquisition. During the warm-up time, the image acquisition software is initialized. Afterwards, the light output port of the lightsource is completely opened and the power is measured. After reaching an output power of 220 mW+/−5 mW, the light source is considered to have reached steady state. The image acquisition system is tested by imaging a standard US Air Force 1951 calibration pattern (FIG. 3). Dark regions should have an intensity of 4.5+/−1 counts/ms and clear regions should have an intensity of 60+/−10 counts/ms. If the intensity values are out of range, a thorough check of the hardware is performed.

Imaging tips are washed with soap and dried with a paper towel. The tips are then placed in a bag, sealed, and autoclaved. Prior to performing data acquisition, a tip is removed from the sterile bag and screwed into place. One sterile tip is used per ex vivo tissue specimen. Once used, the tip is cleaned and sterilized prior to further use.

The spatial resolution of the LUM Imaging Device was determined using an image of a standard US Air Force 1951 resolution target (FIG. 3). Based on the horizontal (top right) and vertical (bottom right) contrast transfer functions and applying the Reyleigh criterion (26.4% contrast), the spatial frequency resolutions are approximately 63 cycles/mm for both axes. This corresponds to a resolution of 16 μm.

The fluorescence to background detection limit of the imaging device was determined by using 6 μm calibrated fluorescent microspheres (similar to those used to calibrate flow cytometry devices). The relative fluorescence intensities from these microspheres range from 0.04% to 100%, providing a wide range of signal-to-background ratios to be tested. Each microsphere solution containing a specific relative fluorescence was diluted to a nanomolar concentration in phosphate buffered saline with a known fluorescence background. Two samples were prepared for each relative fluorescence and the fluorescence emission of ten microspheres on each sample was measured with the device. The limit of fluorescence detection was reached for a signal ratio of single bead fluorescence to background fluorescence of 1.1:1.

In vitro photobleaching experiments have been performed to evaluate the potential degradation of the fluorophore given excessive light activation. The results indicate that the fluorescence signal decays about 5% after five minutes of continuous exposure to the excitation light. The excitation power from the Xenon light source varied 0.1% over thirty minutes. These data demonstrate that the current light source has little effect on fluorophore photobleaching and has excellent stability during the expected timescales of surgical procedures.

Canine Trial

Composition A has been used in a clinical trial in dogs with naturally occurring cancer at Tufts University Cummings School of Veterinary Medicine. Twelve canine patients have completed the trial. Doses of composition A ranged from 0.5 mg/kg to 2.0 mg/kg, which allometrically scales to 0.28 mg/kg and 1.2 mg/kg in humans, respectively. All dogs underwent surgery with no complications. Dogs were monitored at the veterinary hospital for approximately 24 hours prior to surgery and overnight after surgery. Clinical chemistry blood samples taken for the first 8 dogs prior to injection (baseline) and post injection at 24 and 48 hours showed no related adverse effects from composition A. The dog owners have not reported any side effects up to 13 months after injection. Table 1 shows that intraoperative imaging of 49 tissue samples from these dogs correlate 100% with pathology analysis. After the initial gross resection, 11 dogs showed no residual fluorescence in the tumor bed, which was confirmed by pathology. In one dog, the LUM Imaging System detected residual cancer in the tumor bed, which led the surgeon to continue the surgery until no residual fluorescence was detected. Pathology confirmed that after the initial resection, the patient had positive margins but after removal of all the fluorescent tissue, negative margins were obtained. None of these dogs have had a local recurrence up to 13 months after the surgery. FIG. 4 and FIG. 5 show representative images collected during the canine clinical trial.

TABLE 1

|  | Positive fluorescence | Negative fluorescence |
|---|---|---|
| Abnormal Tissue | 19 | 0 |
| Normal Tissue | 0 | 30 |

Studies with Cancer Models in Mice 83 mice have been injected with composition A, including 42 mice with sarcomas, 34 mice with breast cancer, and 7 mice without cancer. For the experiments in the mouse models, the imaging agent is typically injected 6-24 hours prior to the surgery at a dose of 3.52 mg/kg, diluted in 150-200 μL of phosphate buffered saline with a pH of 7.4. No adverse effects have been noted in any of the mice after injections or during the surgical procedures for tumor imaging. One mouse has been injected at 10-fold and another at 25-fold dose of composition A and there were no signs of adverse effects.

Figure 7:
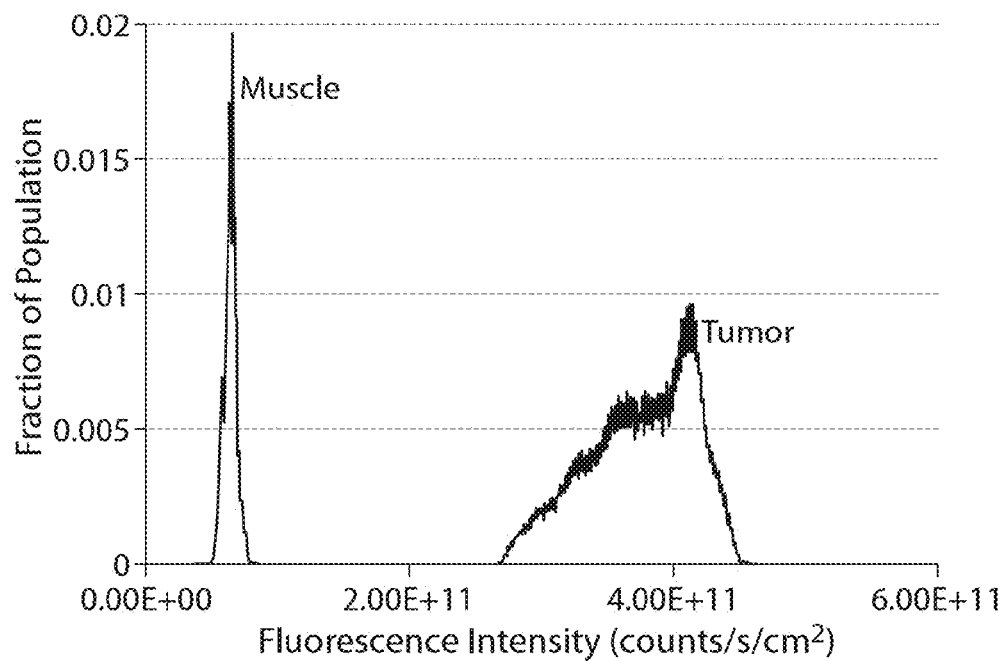
FIG. 7 shows fluorescence intensity histograms from tumor and muscle tissue from FIG. 6 showing a substantial gap (>6 standard deviations from the tumor mean) between the two intensity profiles.

Composition A and the LUM Imaging Device has been tested in genetically engineered mice (*Mus musculus*, 129 sv/Jae) with primary sarcomas. Mice carrying compound conditional LSL-K-ras$^{G12D}$; Trp53$^{Flax/Flax}$ mutations were injected into the muscle with an adenovirus expressing Cre recombinase. As previously described (Kirsch, 2007), these mice developed undifferentiated pleomorphic sarcomas at the site of injection 2 to 3 months later. This mouse model develops lung metastases, similar to sarcoma progression in humans (Kirsch, 2007). The average tumor-to-background (TBR) signal ratio from 12 tumors was 12.8±4.2 (average± standard deviation). Representative images of a primary mouse sarcoma compared to normal muscle following composition A injection are shown in FIG. 6. Histograms of the fluorescence intensity from the same tumor and muscle tissue were separated with no overlap as shown in FIG. 7.

Figure 8:
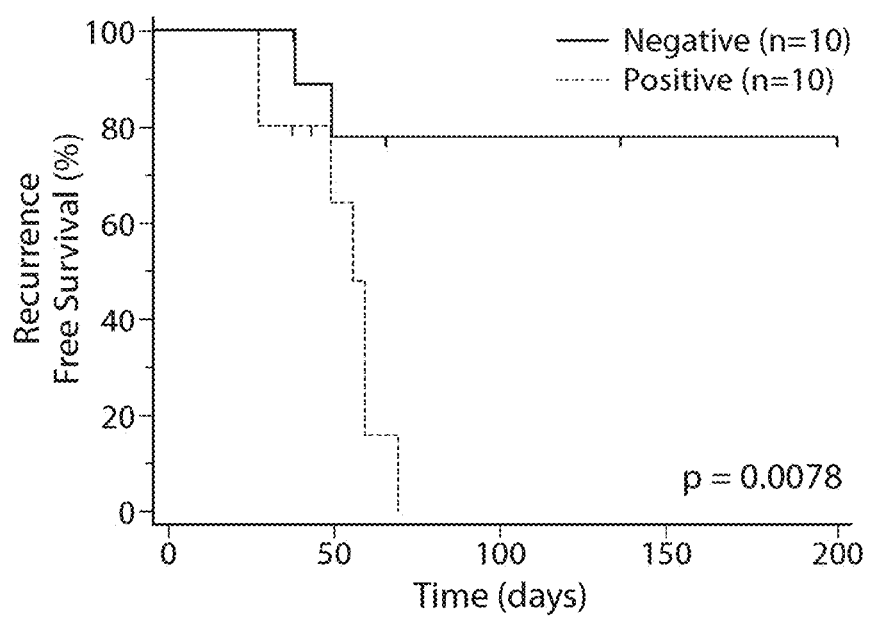
FIG. 8 shows that mice with primary sarcomas injected with composition A that have residual fluorescence in the tumor bed have a high risk of local recurrence. The absence of residual fluorescence in the tumor bed correlates with local control.

Intraoperative imaging of the primary sarcomas were performed using the LUM Imaging Device after injection with composition A. When mice (n=20) developed sarcomas, each tumor was completely resected. The tumor was then imaged and a threshold for residual fluorescence was set as 80% of the minimal signal from the tumor. Then the tumor bed was imaged. If the signal from the tumor bed exceeded the threshold, then the tumor bed was classified as having no residual fluorescence. After composition A injection, the presence of residual fluorescence in the tumor bed correlates with local recurrence (p=0.0078), while tumor beds without residual fluorescence are more likely to remain free of tumor recurrence (FIG. 8).

Figure 9:
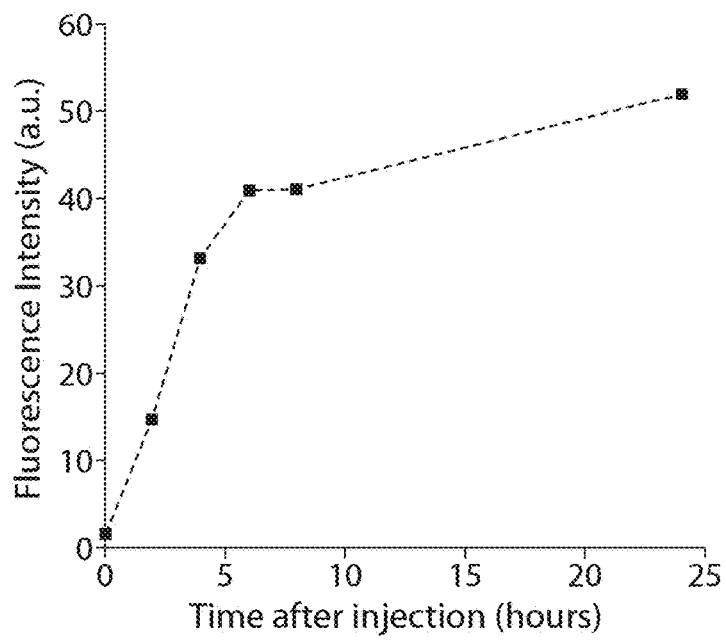
FIG. 9 shows that composition A is activated and accumulates in tumor tissue in mice. Activation of composition A in the tumor was collected by full-body imaging of a mouse using fluorescence molecular tomography (FMT) at 0, 2, 4, 6, 8, and 24 hours after injection.

Imaging studies with the LUM Imaging Device in a xenograft model (MMTV cancer cell line) of breast cancer in FVB mice injected with composition A have also been performed. These experiments demonstrate that composition A effectively labels breast tumors in mice. For these experiments, composition A was injected intravenously at a dose of 3.52 mg/kg. An in vivo time-course activation experiment in this mouse model was performed using fluorescence molecular tomography (FMT) for full body serial imaging. This experiment indicates that fluorescence emission from cleaved composition A can be used to image a breast tumor 6-24 hours after injection in a mouse (FIG. 9).

Figure 10:
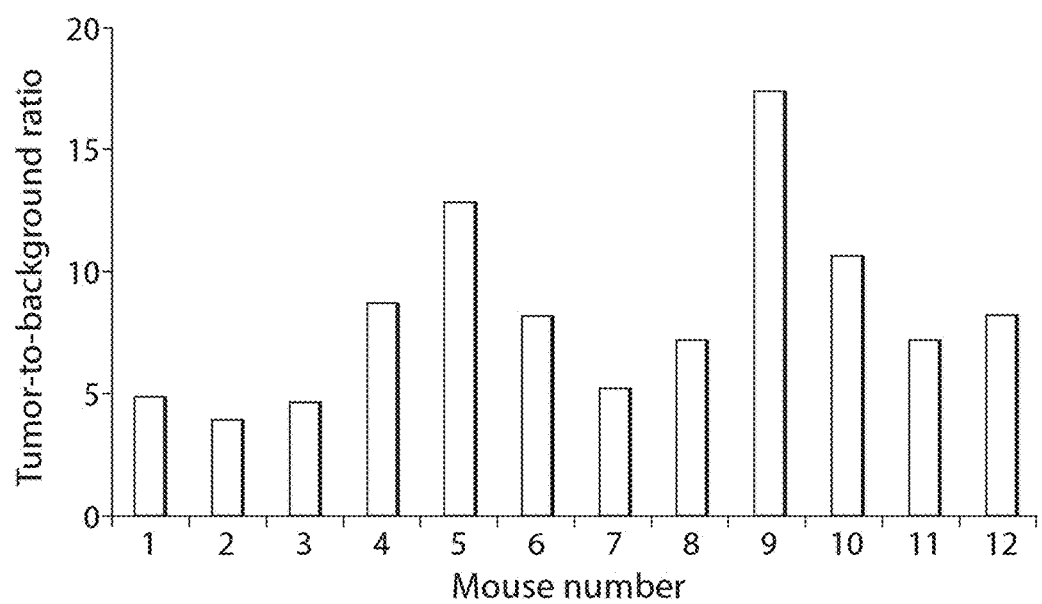
FIG. 10 shows tumor-to-background signals for 12 mice with breast cancer xenografts that were injected with composition A. Resected tumor and muscle (background) were imaged with the LUM Imaging Device 6 hours after injection.
Figure 11:
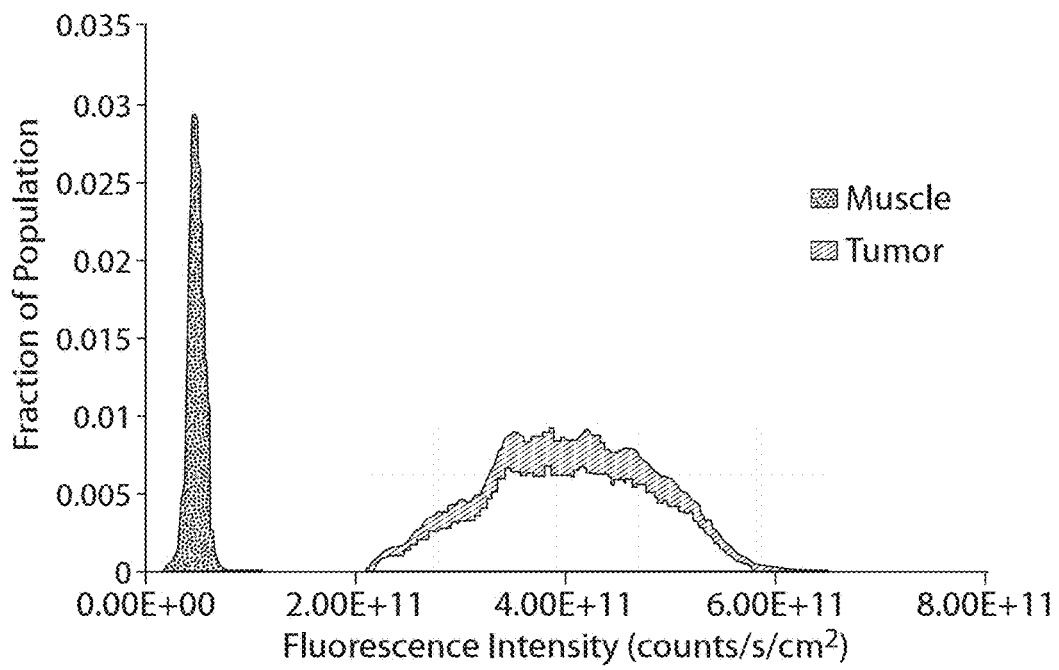
FIG. 11 shows representative fluorescence intensity histograms from tumor and normal (muscle) tissue in a mouse model for breast cancer. Tissue was resected and imaged ex vivo 6 hours after injection with composition A.

Experiments were performed to measure the fluorescence emission rate from breast cancer xenografts and healthy muscle tissue using the LUM Imaging Device. In a cohort of 12 mice with breast cancer xenografts injected with formulated composition A 6 hours prior to surgery, the tumor-to-background (TBR) signal ratio was 8.3±3.1 (average± standard deviation). FIG. 10 shows the TBR from each of the 12 mice demonstrating the high specificity of composition A to label tumors. For most cases, the intensity histograms from both tissues do not overlap (FIG. 11), providing an intensity threshold to discriminate between tumor and healthy tissue.

Taken together, these data from xenograft breast cancer experiments in mice and from primary sarcomas in mice demonstrate that composition A can be used to identify sarcomas and breast cancer compared to normal tissue in vivo. Results with primary sarcomas in mice with composition A demonstrate that this technology can risk-stratify mice for local recurrence.

Cathepsin and Breast Cancer Tissue

Figure 12:
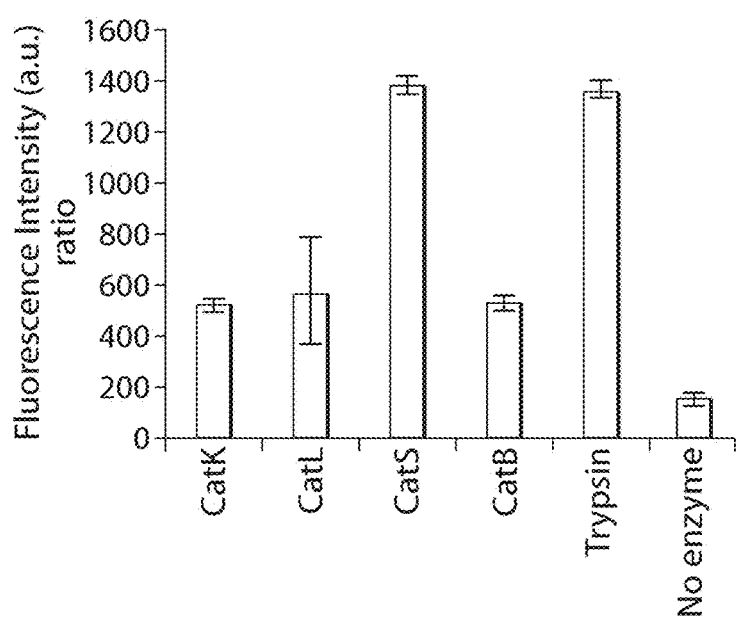
FIG. 12 shows activation of composition A by cathepsins K, L, S and B in an in vitro experiment. Error bars indicate +/− one standard deviation from the mean.

Several reports show over-expression of cathepsin enzymes (B, K, L, and D) in ductal carcinoma in situ as well as in invasive carcinomas (lobular and ductal) (Thomssen et al, 1995; Naidu et al, 1998; Lecaille et al, 2002; Gocheva et al, 2007). Furthermore, Chen et al (2011) demonstrated higher enzymatic activity of cathepsins in breast cancer tissue samples from humans. Also, cathepsin B is typically over-expressed in inflammatory breast cancer, one of the most lethal forms of primary breast cancer with a 3-year survival rate of 40% (Lerebours et al, 2005; Nouh et al, 2011). The peptide sequence which is cleaved in composition A is a pan-cathepsin substrate (FIG. 12). Therefore, it is anticipated that composition A will be activated in human breast cancers.

A canine clinical trial is being conducted to test the efficacy of the system in naturally occurring tumors with similar size of those in humans. One of the cases was a dog with an adenocarcinoma in the mammary gland. Composition A was injected at a dose of 0.5 mg/kg (allometric equivalent to the 3.52 mg/kg dose in mice) and a mastectomy was performed 16 hours after injection. The fluorescence signal from the tumor mass was clearly higher than the signal from surrounding fatty tissue (FIG. 4). Fluorescence emission from each of these tissues correlated perfectly with the corresponding histopathology assessment of the presence/absence of cancer cells.

The data gathered from the literature and from the studies in mice and dogs described above indicate that cathepsin proteases are active in breast cancer when compared to normal tissue and that the imaging agent composition A is activated in breast cancers in vivo.

Human Studies

Figure 13:
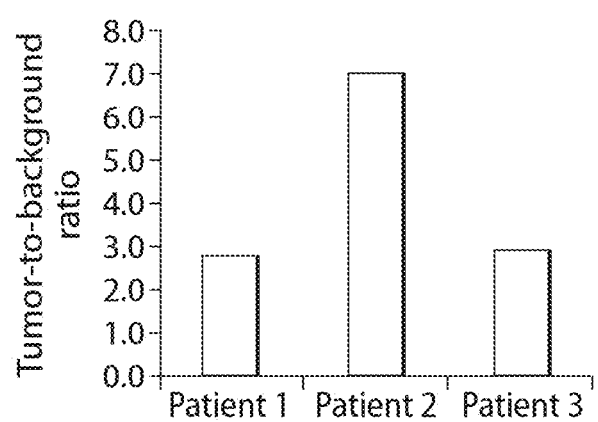
FIG. 13 shows tumor-to-background ratios for the first three humans enrolled in the Phase I clinical trial to test the safety and efficacy of composition A.

At the time of preparing this document, a Phase I clinical trial (NCT01626066) in humans is currently underway to evaluate the safety of composition A in breast cancer and sarcoma patients and its efficiency to label human cancer. The primary objective of the Phase I study is to identify a recommended safe dose of composition A for labeling tumor to be then used in a Phase II clinical trial. Patients are injected with composition A (dose of 0.5 mg/kg, 1.0 mg/kg or 1.5 mg/kg) 24-36 hours prior to surgery and monitored for vital signs and pharmacokinetic measurements. Patients undergo standard of care surgery; however, all the resected tissue is imaged at the pathology suite using the LUM Imaging System (FIG. 1) to measure the fluorescence signal from tumor and adjacent normal tissue. To date, three sarcoma patients have completed the Phase I study at a dose of 0.5 mg/kg and no adverse events were observed. Resected tissues from these patients were imaged using the LUM Imaging System and was determined an average tumor-to-background signal ratio (TBR) of 4:1 (FIG. 13) with a variance of approximately 20% and no overlap form histograms between tumor and normal tissue. Based on these data, a sensitivity and specificity of 99% is predicted. Thus, these TBR's are sufficient to clearly identify tumor cells from normal adjacent tissue without ambiguity. Composition A (LUM 015) has been compared to a different imaging agent, VM249, using the LUM Imaging Device. VM249 uses a fluorophore that can image deeper tissue, beyond 5 mm., As can be seen from the Table below, LUM 015 unexpectedly had 100% sensitivity, whereas VM249 had 50% sensitivity.

| | LUM015 | VM249 |
|---|---|---|
| Absorption max (nm) | 649 | 673 |
| Emission max (nm) | 670 | 707 |
| Sensitivity/specificity in canine trial (pathology endpoint) | 100% and 100% | 50% and 100% |

What is claimed is:

1. A compound of formula I:

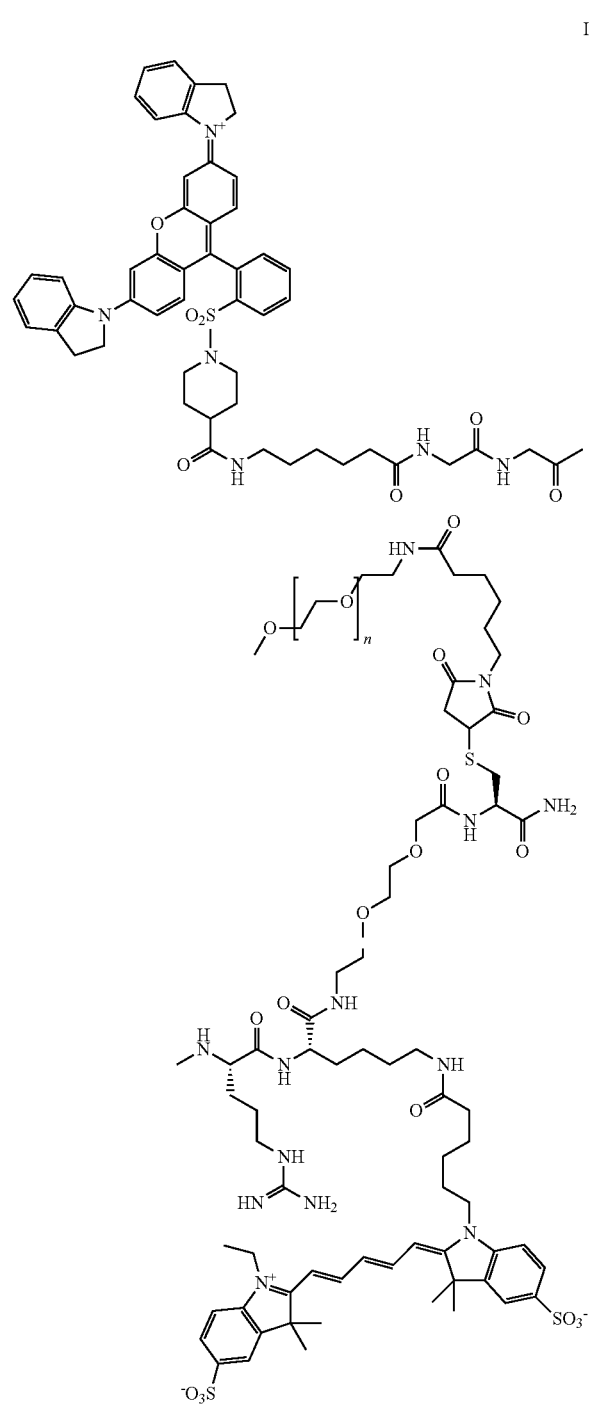

or a pharmaceutically acceptable salt thereof,
wherein n is an integer between 400 and 500, inclusive.

2. The compound of claim 1, wherein n is an integer between 440-460, inclusive.

3. The compound of claim 1, wherein the portion of the molecule defined by brackets (mPEG portion) is about 20,000 g/mol in molecular weight.

4. The compound of claim 1, wherein the formula is:

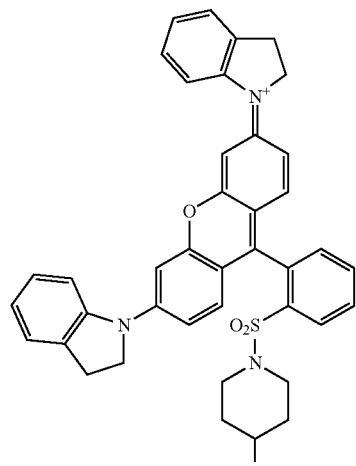
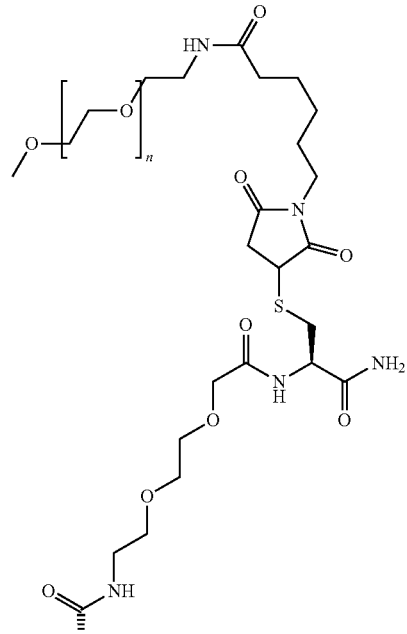
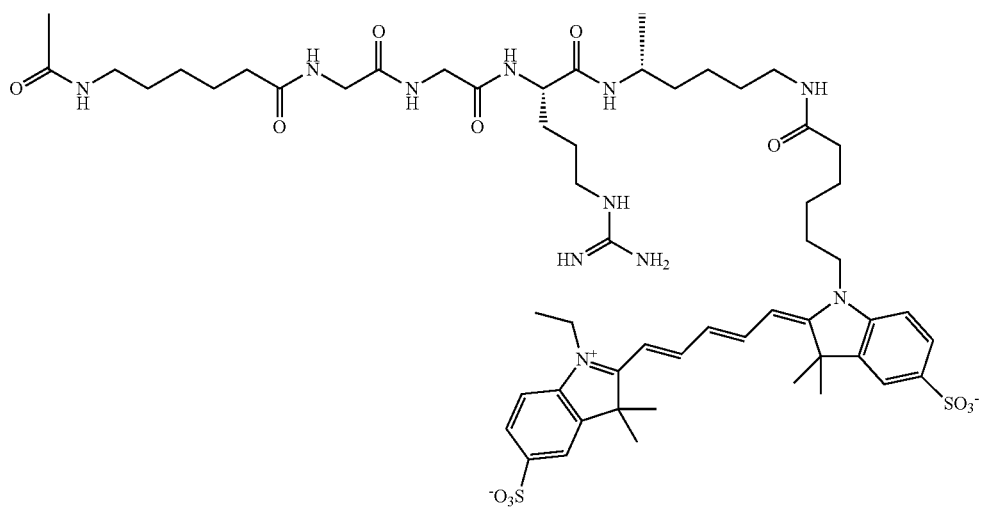

or a pharmaceutically acceptable salt thereof.

5. The compound of claim 1, wherein the compound is provided as an acetate salt.

6. A composition comprising one or more compounds of claim 1 or a pharmaceutically acceptable salt thereof.

7. A composition comprising a plurality of compounds of claim 1 or a pharmaceutically acceptable salt thereof.

8. The composition of claim 7, wherein the average value of n for the compounds in the composition is between 440-460, inclusive.

9. The composition of claim 7, wherein the average value of n for the compounds in the composition is about 450.

10. The composition of claim 7, wherein the average molecular weight of the mPEG portion of the molecules,

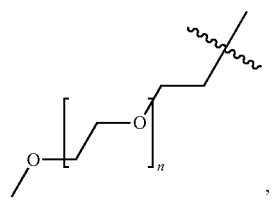

is about 20,000 g/mol.

11. A compound of formula II:

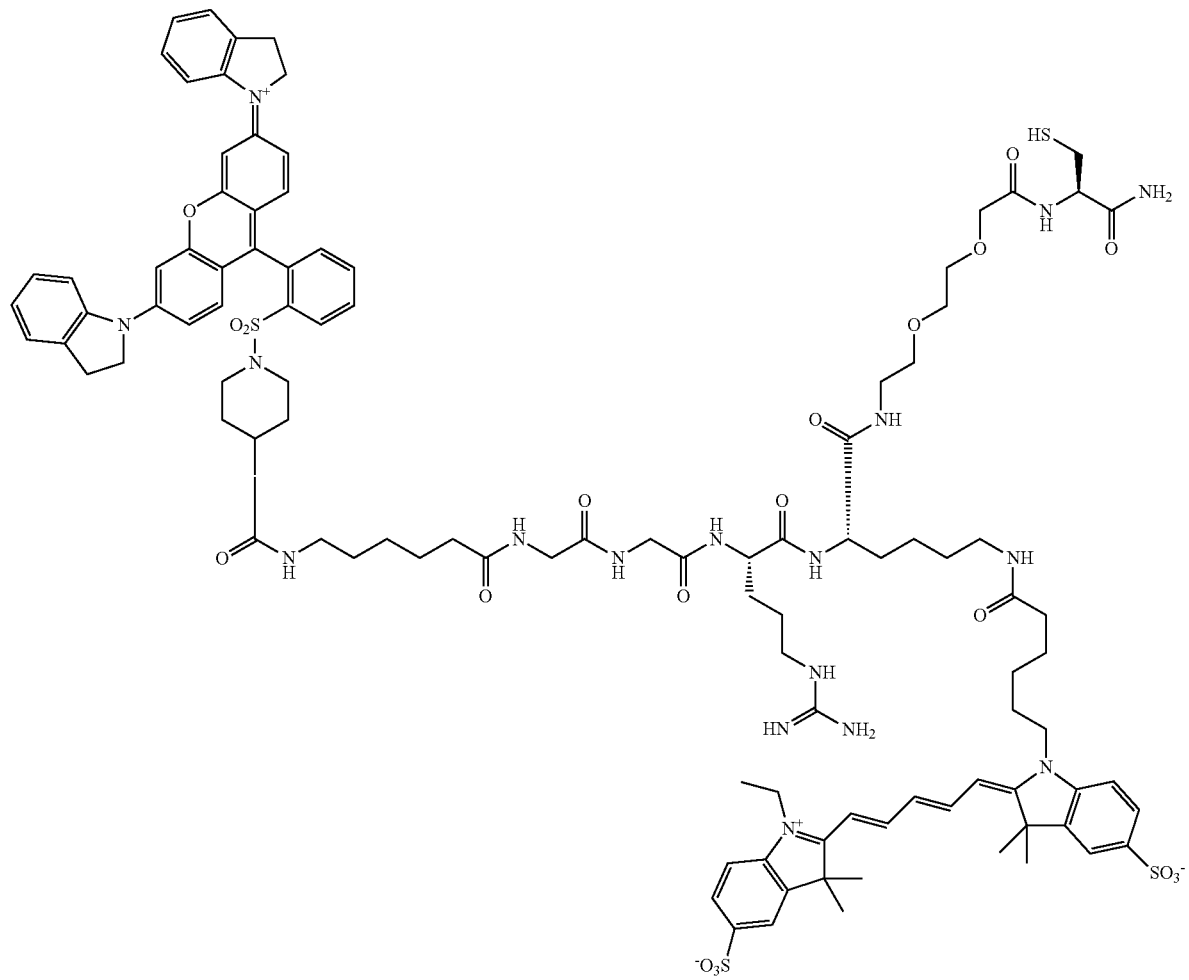

or a salt thereof.

12. An in-vivo method for spatially determining tissue heterogeneity of tissue of a subject comprising:
 (a) administering a composition of claim 6 to the subject; and
 (b) obtaining after said administration step an in-situ image of said tissue.

13. The in-vivo method of claim 12, wherein the image is obtained using an imaging system having pixels with a field of view, and wherein the field of view of each pixel when said image is obtained is one cell or less than one cell.

14. The method of claim 12, wherein the composition is administered systemically and the image is obtained between 12 and 72 hours after the composition is administered.

15. The method of claim 12, wherein the composition is administered systemically and the image is obtained between 12 and 36 hours after administration.

16. The method of claim 12, wherein the image distinguishes between diseased cells and healthy cells within 5 mm, 4 mm, 3 mm, 2 mm, or even 1 mm from the surface of the tissue.

17. The method of claim 16, wherein the image does not distinguish between diseased cells and healthy cells that are deeper than 5 mm, 6 mm, 7 mm, 8 mm, 9 mm, or 10 mm from the surface of the tissue.

18. The method of claim 12, wherein the image distinguishes between diseased cells and healthy cells, and the diseased cell is a cancer cell.

19. The method of claim 12, wherein the tissue is a tissue bed left behind after tumor resection.

20. The method of claim 12, wherein the subject is a human.

21. The method of claim 12, wherein the composition is administered topically in-vivo.

* * * * *